United States Patent
Kang et al.

(10) Patent No.: US 9,602,952 B2
(45) Date of Patent: Mar. 21, 2017

(54) SELF-DIRECT M2M (MACHINE-TO-MACHINE) COMMUNICATION BASED USER'S DAILY ACTIVITY LOGGING AND ANALYZING SYSTEM WITH WEARABLE AND PERSONAL MOBILE DEVICES

(71) Applicant: KYUNGPOOK NATIONAL UNIVERSITY INDUSTRY-ACADEMIC COOPERATION FOUNDATION, Daegu (KR)

(72) Inventors: Soon Ju Kang, Daegu (KR); Sang Ho Jun, Daegu (KR); Kyung Chun Lee, Incheon (KR); Ki Eun Seong, Daegu (KR); Hyeong Gon Jo, Gyeongsangbuk-do (KR); Jae Hee Seo, Busan (KR); Cheol Soo Ahn, Daegu (KR); Seong Wook Han, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 0 days.

(21) Appl. No.: 14/436,781

(22) PCT Filed: Oct. 18, 2013

(86) PCT No.: PCT/KR2013/009336
§ 371 (c)(1),
(2) Date: Apr. 17, 2015

(87) PCT Pub. No.: WO2014/062030
PCT Pub. Date: Apr. 24, 2014

(65) Prior Publication Data
US 2016/0183029 A1 Jun. 23, 2016

(30) Foreign Application Priority Data

Oct. 19, 2012 (KR) .................. 10-2012-0116672
Apr. 19, 2013 (KR) .................. 10-2013-0043556

(51) Int. Cl.
*H04W 72/04* (2009.01)
*H04W 4/00* (2009.01)
(Continued)

(52) U.S. Cl.
CPC ........ *H04W 4/005* (2013.01); *G06F 19/3418* (2013.01); *G06Q 50/22* (2013.01);
(Continued)

(58) Field of Classification Search
CPC . H04W 4/005; H04W 4/008; H04W 72/0453; H04B 17/318; G06F 19/3406; G06F 19/3418; G06Q 50/22
See application file for complete search history.

(56) References Cited

U.S. PATENT DOCUMENTS

| | | | |
|---|---|---|---|
| 2012/0092157 A1* | 4/2012 | Tran | G06F 19/3418 340/539.12 |
| 2012/0223833 A1* | 9/2012 | Thomas | G06F 19/3418 340/539.12 |

(Continued)

FOREIGN PATENT DOCUMENTS

| | | |
|---|---|---|
| JP | 2008-234009 A | 10/2008 |
| KR | 10-2002-0091655 A | 12/2002 |

(Continued)

OTHER PUBLICATIONS

International Preliminary Report on Patentability regarding corresponding PCT Application No. PCT/KR2013/009336, dated Apr. 30, 2015.

*Primary Examiner* — Bobbak Safaipour
(74) *Attorney, Agent, or Firm* — Lewis, Reese & Nesmith, PLLC

(57) ABSTRACT

The present invention relates to a heath care system having proximity-based neighbor device wake-up and automatic user identification function, a method for automatic logging of user's daily activity history, and a method for managing a user activity pattern, and the system comprises: a health or wellness service unit; and an user terminal. The health or wellness service unit transmits a wake-up signal for changing a state of the user terminal from a sleep state into a wake-up state, a low frequency (LF) signal for identifying a physical distance and direction between the health or wellness service unit and the user terminal, and a measured biological signal of a measuring object. The user terminal receives the biological signal, the wake-up signal, and the LF signal through bidirectional wireless communication with the health or wellness service unit, and transmits a terminal identification (ID) and a received signal strength indication (RSSI) corresponding to the received LF signal.

16 Claims, 17 Drawing Sheets

(51) Int. Cl.
*G06F 19/00* (2011.01)
*G06Q 50/22* (2012.01)
*H04B 17/318* (2015.01)

(52) U.S. Cl.
CPC .......... *H04B 17/318* (2015.01); *H04W 4/008* (2013.01); *H04W 72/0453* (2013.01); *G06F 19/3406* (2013.01)

(56) References Cited

U.S. PATENT DOCUMENTS

2013/0176069 A1* 7/2013 Leong .................... B60R 25/24
327/517
2015/0044969 A1* 2/2015 Tucker .................... H04B 7/26
455/41.2

FOREIGN PATENT DOCUMENTS

| KR | 10-2005-0022000 A | 3/2005 |
|---|---|---|
| KR | 10-0601981 B | 7/2006 |
| KR | 10-0715671 B | 5/2007 |
| KR | 10-0763175 B | 10/2007 |
| KR | 10-1058910 B | 8/2011 |
| KR | 10-1188565 B | 10/2012 |
| KR | 10-1243300 B | 3/2013 |
| KR | 10-1369317 B | 3/2014 |

* cited by examiner

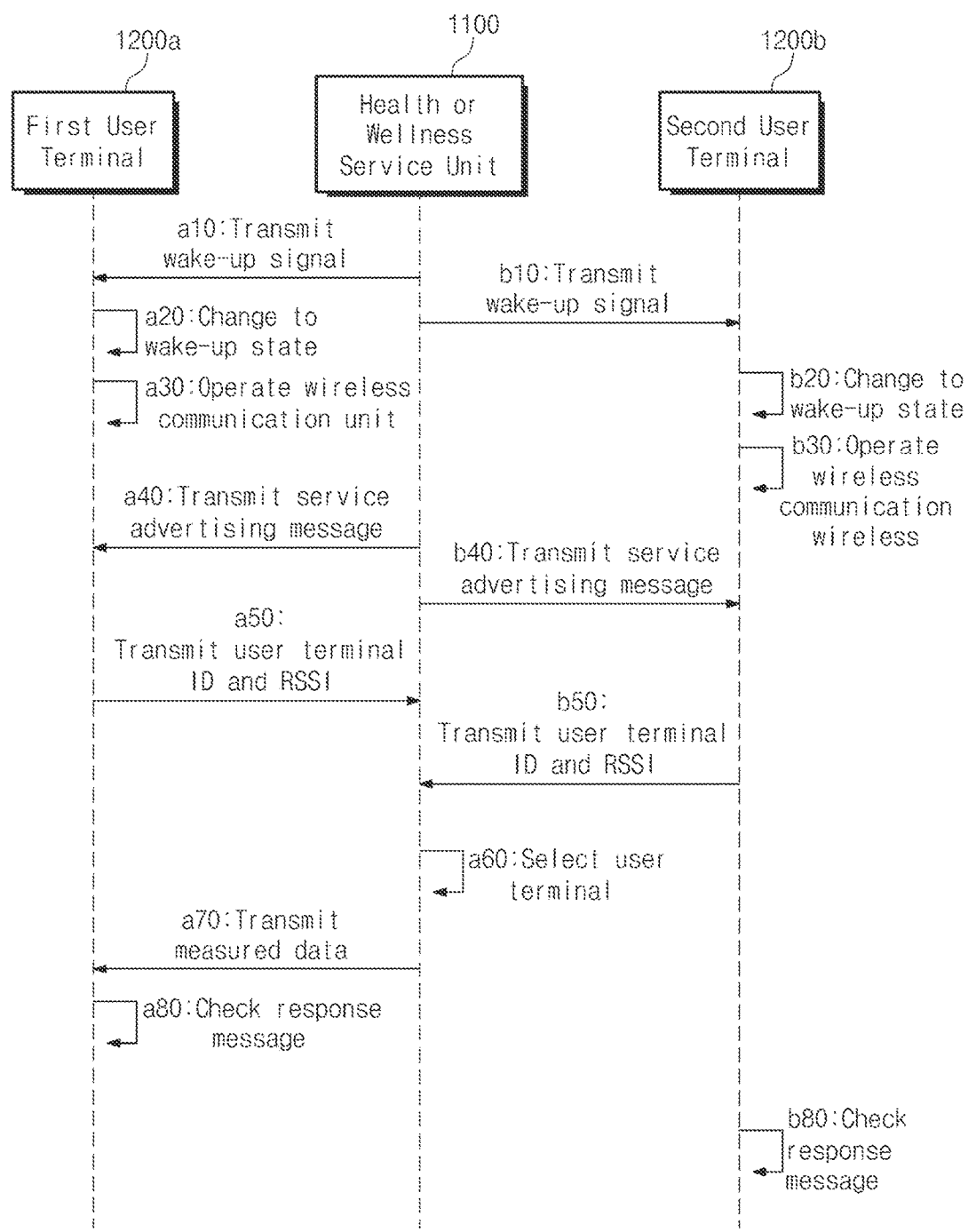

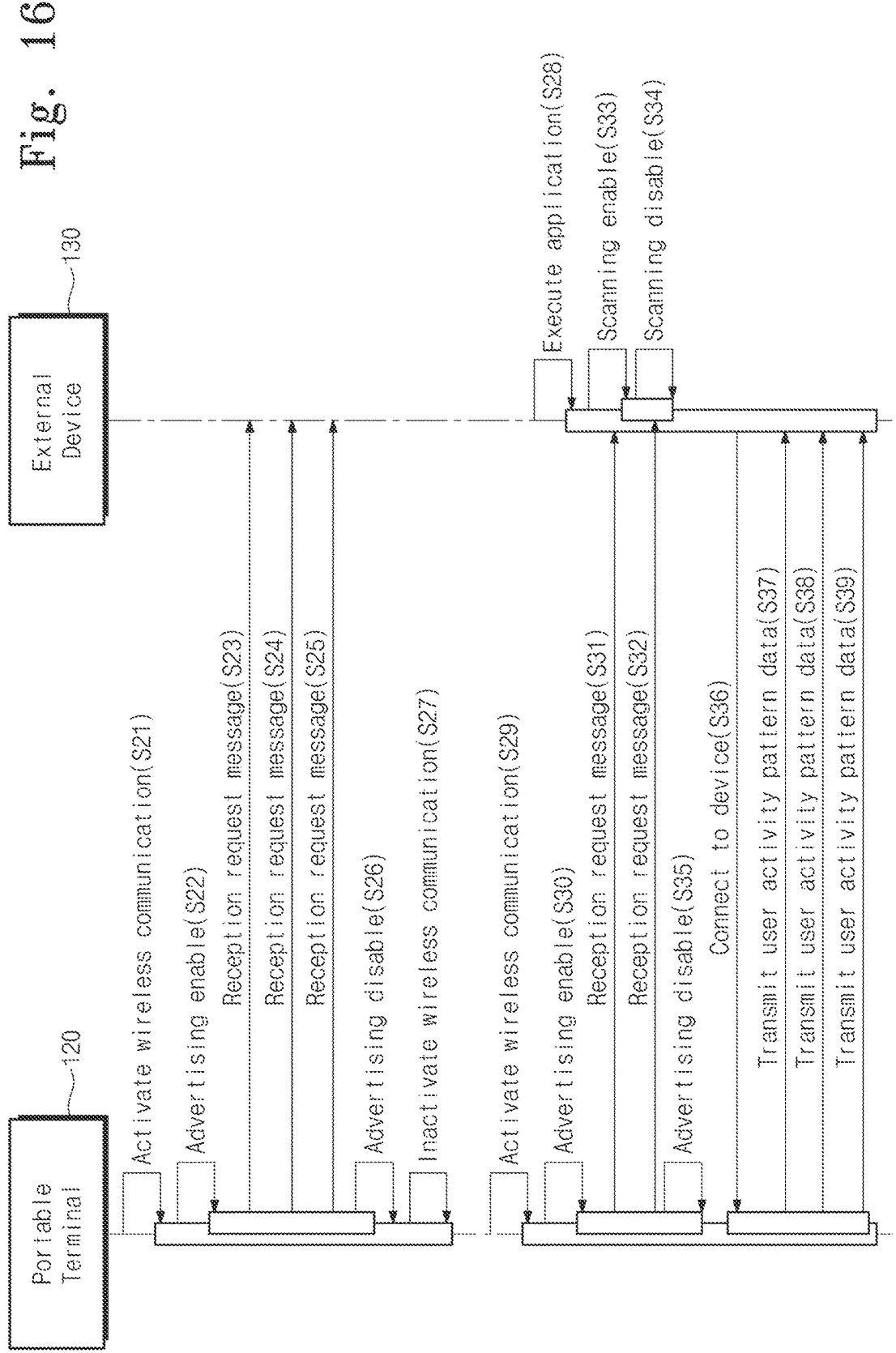

SELF-DIRECT M2M (MACHINE-TO-MACHINE) COMMUNICATION BASED USER'S DAILY ACTIVITY LOGGING AND ANALYZING SYSTEM WITH WEARABLE AND PERSONAL MOBILE DEVICES

CROSS-REFERENCE TO RELATED APPLICATIONS

This U.S. non-provisional patent application claims priority under 35 U.S.C. §119 of Korean Patent Application Nos. 10-2012-0116672, filed on Oct. 19, 2012, and 10-2013-0043556, filed on Apr. 19, 2013, the entire contents of which are hereby incorporated by reference.

TECHNICAL FIELD

The present invention disclosed herein relates to a heath care or wellness system having proximity-based neighbor device wake-up and automatic user identification function, a method of logging and analyzing a user's daily life activity history, and a method of automatic alerting and reminding a user's abnormal activity pattern.

BACKGROUND ART

With the recent rapid development of an economic level, a desire to enhance the quality of life increases and such a desire is represented as great interest in personal health or wellness.

With the significant enhancement of overall health and medical treatment conditions of medicine and medical devices including medical knowledge, a national health level has been steadily improved. For example, an average lifetime has been extended but, a chronic degenerative disease such as an adult disease has increased rapidly due to a change in lifestyle such as industrialization, aging or urbanization.

As represented in a recent research result that various chronic degenerative diseases are related to a personal lifestyle, everybody agrees that the best way to maintaining personal health is steady management and usual examination.

In particular, health related content based on information communication infrastructure and information communication technology is recently spread, so it may be seen that an information technology-bio technology (IT-BT) hybrid technology age has arrived.

Anybody may carry or wear a high-performance micro computer through a rapid technological development, and with the recent, broad distribution of smart phones or smart watch(wearable devices) and the construction of a mobile network, a ubiquitous age in which a user may connect to a network anytime or anywhere has arrived. For example, with the approach of a ubiquitous age that is a network age that has high-performance computing-power devices such as wearable devices(such as smart watch) with smart phones and uses theses devices arrives, service areas that are typically provided are also expanded gradually in range.

Silver industry and medical service industry fields develop in order to keep pace with the aging society, and thus if a ubiquitous wearable technology and a health care technology are combined, a patient may manage his or her health for oneself at home even if he or she does not necessarily go to the hospital. With the technological development and an increase in lifetime, a medical service industry field has further developed and devices for effectively providing such a medical service have been invented.

Typically, since most of medical services fail to utilize the advantage of a high-performance mobile terminal and most of users that use the medical services are old, there is a difficulty in operating an interface to a mobile terminal and thus there is no dramatic effectiveness.

For example, in the case of a dementia patient, he or she has a difficulty in managing his or her health for oneself without a guardian and in some cases, a guardian may not take care of the dementia patient due to the reason for making ends meet. Accordingly, there is a need for a system that provides a big help with a user's daily activity even without a complex user's operation.

Also, when a medical service is provided by using a communication scheme such as Wi-Fi, 802.15.4 MAC, or Bluetooth scheme, there is a limitation in that the precision in location identification of a mobile terminal in a narrow area of 0.1 m to 3 m is low.

That is, a complex calculation is needed in order to accurately measure the location of a mobile terminal, but related art has a limitation in performing the calculation by using a low-power micro control unit (MCU) and thus there is a limitation in that since the related art may not accurately identify the location when there is a wire wall or an obstacle, it is not appropriate for applying to an indoor medical service.

Also, when providing a medical service to a portable personal mobile terminal, the related art has a limitation in that power consumption significantly increases.

That is, when a location is identified by using a general RF signal strength, the frequent transmission and reception of RF signals are needed between a fixed device and a device for identifying a location in which case, a power consumption amount is significantly greater than a fundamental power consumption amount because power consumption increases in proportion to a increase in the number of times transmission and reception are performed.

A limitation that may appear when providing various services by using mobile terminals performing short-range communication is that the power consumption of a portable terminal is great because an electric wave needs to be continuously transmitted to around the portable terminal in order to monitor the approach of another terminal that attempts to establish a communication network. This operation reduces the charging and replacement cycle of a battery and causes significant inconvenience in use.

DISCLOSURE OF THE INVENTION

Technical Problem

The present invention provides user's daily activity logging and analyzing system having physical proximity based neighbor device wake-up and identification function, a method for automatic archiving user's vital signals measured from health or wellness service unit, and a method of automatic logging and analyzing user's daily activity information in his/her wearable or mobile device that efficiently manage the power consumption of a user terminal through a wake-up function of the user terminal, automatically receive a biological signal from a health or wellness service or transmit a packet formed by adding a user ID to a measured biological signal to an operator server to manage user's health even when a user does not separately operate the user terminal.

The present invention may minimize power consumption by the proximity-based neighbor device wake-up function. Due to the function, the present invention never require any user's strong intervention to use or configure the wearable or mobile devices, and also identify a user's abnormal activity pattern only with a user's daily activity.

The present invention helps a user activity and manages a user activity pattern by reminding the alarm or informing a guardian or a medical specialist when a user does not follow an activity pattern defined in a pre-schedule activity list, or an abnormal activity pattern that may cause a risky situation is sensed by the wearable device itself.

The present invention enables a user's guardian or a medical specialist to remotely manage a user activity pattern though a guardian's mobile terminal or a hospital-site patient management system.

Technical Solution

Embodiments of the present invention provide health care systems including proximity-based neighbor device wake-up and automatic user identification function, the health care system including: a health or wellness service unit; and an user terminal, wherein the health or wellness service unit transmits a wake-up signal to change a state of the user terminal from a sleep state to a wake-up state, a low frequency (LF) signal for identifying a direction and a physical distance between the health or wellness service unit and the user terminal, and a measured biological signal of a subject, and wherein the user terminal receives the biological signal, the wake-up signal and the LF signal through bidirectional wireless communication with the health or wellness service unit, and transmits a terminal identification (ID) and a received signal strength indication (RSSI) corresponding to the received LF signal.

In other embodiments of the present invention, methods of automatic logging of user's daily activity history include receiving a wake-up signal to change the state of a user terminal from a sleep state to a wake-up state, and an LF signal for identifying a location of the user terminal, from a health or wellness service unit; sensing the wake-up signal, generating interrupt and changing the user terminal from the sleep state to the wake-up state; transmitting an user terminal ID, a RSSI of the received LF signal and a direction information of the received LF signal, to the health or wellness service unit; selecting a user terminal using the transmitted RS SI value and the transmitted direction information of the received LF signal; and transmitting measured data on a subject to the selected user terminal.

In still other embodiments of the present invention, user's daily activity logging and analyzing systems include a terminal installed at one or more device sides provided in a user activity area, the terminal including a sensor sensing a user's usage action to the device; and a portable terminal receiving activity data corresponding to the usage action from the terminal to construct user activity pattern data, wherein the terminal includes a LF transmitter that transmits a wake-up signal to the portable terminal when the usage action is sensed, and the portable terminal includes a LF receiver that receives the wake-up signal from the LF transmitter, and changes from a sleep mode to a wake-up mode according to the wake-up signal to receive the activity data from the terminal.

In some embodiments, the terminal may operate in a low-power standby mode after the activity data is transmitted to the portable terminal until a new usage action is sensed, and the portable terminal may change from the wake-up mode to the sleep mode after the activity data is received from the terminal.

In other embodiments, the sensor may include at least one selected from a hall sensor, a piezo sensor, a photo sensor, a loadcell, a thermal sensor, an angular sensor, and an ammeter.

In still other embodiments, the portable terminal may further include: a time measurement module measuring time information; and a processor combining an ID of the portable terminal, the activity data, and time information corresponding to the activity data, in one data packet to constructing the user activity pattern data.

In even other embodiments, the portable terminal further includes a wireless communication unit broadcasting request data including the ID of the portable terminal in the wake-up mode, and the terminal may further include a wireless transmission unit transmitting the activity data to the portable terminal in response to the request data.

In yet other embodiments, the portable terminal may further include a state control unit activating or deactivating a wireless communication function of the wireless communication unit in a preset cycle, and the wireless communication unit broadcasts a reception request message while the wireless communication function is activated, sets a wireless network in response to an acknowledgement message from an external device corresponding to the reception request message and transmits the user activity pattern data to the external device.

In further embodiments, the portable terminal may further include a schedule management unit that provides a notification function at a time corresponding to each schedule on the schedule management list according to a preset schedule management list.

In still further embodiments, the processor may check whether the user activity pattern data matches the schedule management list, and generate an alarm signal or transmits an alarm message to the external device by controlling the wireless communication unit when the user activity pattern data does not match the schedule management list or an abnormal activity pattern is sensed.

In even further embodiments, the wireless communication unit may receive a schedule management message from the external device, and the schedule management unit may update the schedule management list according to the schedule management message.

In yet further embodiments, the schedule management unit may generate a wake-up event at a time corresponding to each schedule, the portable terminal may change to a wake-up mode according to the wake-up event and transmit a control message to the terminal on a device side corresponding to each schedule, and the terminal may receive the control message, sense the approach of the portable terminal, and communicate with the control unit of the device to automatically operate the device according to the control message.

In much further embodiments, the external device may receive an SMS command message from an external mobile terminal, read the SMS command message and transmit a corresponding control command signal to the portable terminal.

In still much further embodiments, the SMS command message may include a meta script, a command, an ID of a device to be controlled, and a control command execution time, and the external device may identify the meta script and transmit the control command signal corresponding to the command to the portable terminal.

In even much further embodiments, the portable terminal may modify the schedule management list, transmit a control message for automatically operating the device to the terminal, or transmit the user activity pattern data to the external device or the external mobile terminal, according to the control command signal.

In even other embodiments of the present invention, user's daily activity logging and analyzing devices include a portable terminal receiving activity data corresponding to a user's usage action to a device from each terminal of one or more device sides provided in a user activity area and constructing user activity pattern data, the portable terminal receiving a wake-up signal corresponding to the usage action from the terminal, changing from a sleep mode to a wake-up mode according to the wake-up signal and receiving the activity data from the terminal.

In some embodiments, the portable terminal may check whether the user activity pattern data matches a preset schedule management list, and generate an alarm signal or transmits an alarm message to an external device when the user activity pattern data does not match the schedule management list or an abnormal activity pattern is sensed.

In other embodiments, the portable terminal may generate a wake-up event at a time corresponding to the schedule management list, change to a wake-up mode according to the wake-up event and transmit a control message for automatically operating the device to the terminal of the device side.

In yet other embodiments of the present invention, methods of logging a user's activity history include sensing a user's usage action to one or more devices, the one or more devices being provided in a user activity area, to transmit a wake-up signal to a portable terminal; changing the portable terminal from a sleep mode to a wake-up mode according to the wake-up signal; transmitting activity data corresponding to the user's usage action from the device side to the portable terminal; and constructing user activity pattern data using the activity data by the portable terminal.

In some embodiments, the method may further include checking by the portable terminal whether the user activity pattern data matches a preset schedule management list; sensing an abnormal activity pattern; and generating an alarm signal or transmitting an alarm message to an external device, when the user activity pattern data does not match the schedule management list or the abnormal activity pattern is sensed.

In other embodiments, the method may further include generating, by the portable terminal, a wake-up event at a time corresponding to each schedule on the schedule management list; changing the portable terminal to a wake-up mode according to the wake-up event and transmitting a control message to a device side corresponding to each schedule; and automatically operating the device according to the control message.

In still other embodiments, the method may further include receiving, by the external device, an SMS command message including a meta script and a command from an external mobile terminal; identifying the meta script and transmitting a control command signal corresponding to the command to the portable terminal, by the external device; and modifying the schedule management list, transmitting a control message for automatically operating the device to the device side, or transmitting the user activity pattern data to the external device or the external mobile terminal, by the portable terminal, according to the control command signal.

Advantageous Effects

According to an embodiment of the present invention, since a wearable terminal is linked with a device needed for a daily life at low power, it is possible to collect and accumulate data at a low power even if a user is not good at operating an electronic device. Also, it is possible to raise data utilization by transmitting data accumulated in the portable terminal to a personal mobile terminal or a hospital server, and furthermore, the automatic control of an electronic device is also possible. Also, by providing a service for comparing a user activity pattern with a schedule management list and analyzing them to sound the alarm to a user or report an analysis result to a guardian or a medial specialist, it is possible to provide various programs for managing users' health and it is possible to quickly cope with an emergency situation.

According to an embodiment, it is possible to efficiently manage the power consumption of a user terminal through a wake-up function of the user terminal.

Also, according to an embodiment of the present invention, since an RSSI corresponding to an LF signal belonging to an LF band is transmitted to the health or wellness service unit and location information is collected such as a direction and a physical distance between the health or wellness service unit and the user terminal, it is possible to more easily identify a location.

Also, according to an embodiment of the present invention, since a user may automatically receive a biological signal measured from the health or wellness service unit even though a user does not perform a separate operation on the user terminal, the user may manage a physical index history more easily.

Also, according to an embodiment of the present invention, it is possible to minimize power consumption without performing a complex user's operation and identify a user activity pattern only with a user's daily activity.

Also, according to an embodiment of the present invention, the present invention may help a user activity and manage a user activity pattern by sounding the alarm or letting a guardian or a medical specialist know when a user does not follow an activity pattern defined in a schedule management list or an abnormal activity pattern that may cause a risky situation is sensed.

Also, according to an embodiment of the present invention, a user's guardian or a medical specialist may remotely manage a user activity pattern though a guardian's mobile terminal or outside the hospital.

The effects of the present invention are not limited the above-described effects. Other effects not mentioned will be clearly understood by a person skilled in the art from the disclosure and the accompanying drawings.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings:

FIG. 3 represents the sequence diagram of a protocol for providing a health care service between the health or wellness service unit and the user terminal of the present invention;

FIG. 16 is a flow chart of steps S13 and S14 shown in FIG. 15.

MODE FOR CARRYING OUT THE INVENTION

Other advantages and features of the present invention, and implementation methods thereof will be clarified through following embodiments described in detail with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to a person skilled in the art. Further, the present invention is only defined by scopes of claims.

Although some terms are not defined, all the terms used herein (including technology or science terms) have the same meanings as those generally accepted by typical technologies in the related art to which the present invention pertains. The terms defined in general dictionaries may be construed as having the same meanings as those used in the related art and/or the present disclosure and even when some terms are not clearly defined, they should not be construed as being conceptual or excessively formal. General descriptions of known configurations may be left out in order not to obscure the subject matter of the present invention.

The term "unit" used throughout the specification may mean a unit for processing at least one function or operation. For example, it may mean software or a hardware component such as an FPGA or an ASIC. However, the term "unit" is not limited to the software or the hardware. The term "unit"may be configured in an addressable storage medium or may be configured to operate one or more processors. Thus, as an example, the "unit" includes components such as software components, object-oriented software components, class components, and task components; processes, functions, attributes, procedures, sub routines, program code segments, drivers, firmware, micro codes, circuits, data, DBs, data structures, tables, arrays and variables. A function provided in the "unit" may be divided into sub components or may be provided through integration with another "unit".

Figure 1:
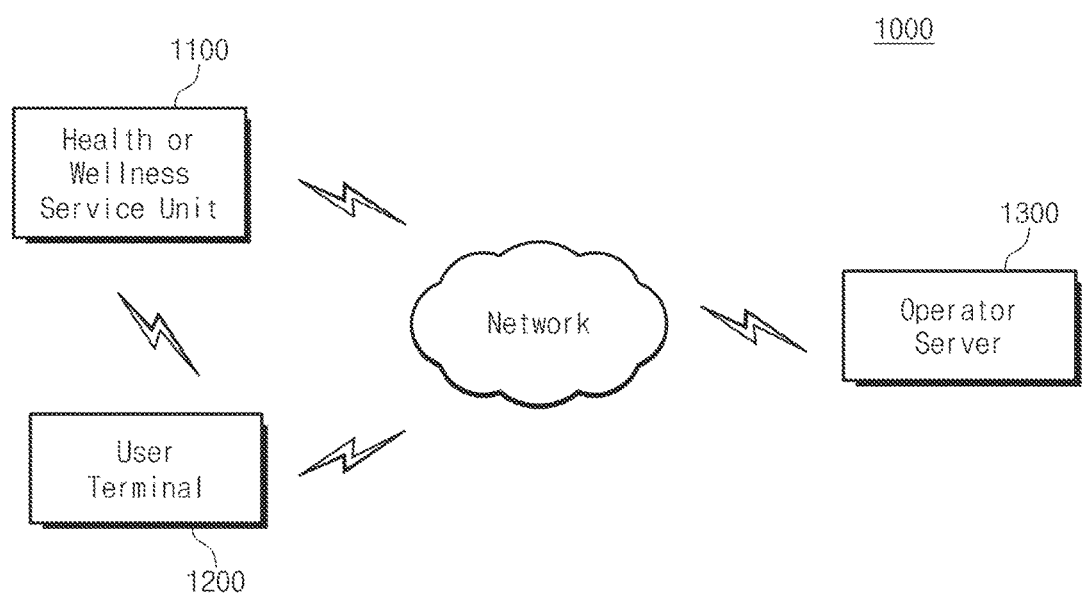
FIG. 1 shows a health care system including proximity-based neighbor device wake-up and automatic user identification function according to the present invention.

FIG. 1 shows a health care system including proximity-based neighbor device wake-up and automatic user identification function according to the present invention.

Referring to FIG. 1, a health care system 1000 including proximity-based neighbor device wake-up and automatic user identification function according to the present invention includes a health or wellness service unit 1100, a user terminal 1200 and an operator server 1300.

The health or wellness service unit 1100 measures a biological signal due to the electrical change, biochemical change, physical momentum, environmental change of a body on or in the vicinity of a subject body. In this case, a measured biological signal is transmitted to the user terminal 1200 by using proximity-based neighbor device wake-up and automatic user identification function.

In this example, the biological signal means multiple medical data such as a blood pressure, pulse rate, electrocardiogram, body temperature and weight of a subject body.

Being transmitted by using proximity-based neighbor device wake-up and automatic user identification function means that measured medical data is automatically transmitted to the user terminal 1200 even if a subject does not separately operate the user terminal 1200.

For example, even though a user does not perform a separate operation on the user terminal 1200, the user terminal 1200 automatically becomes a wake up state in response to a service advertising message transmitted from the health or wellness service unit 1100.

Also, when a corresponding service is preset on the user terminal 1200, a user identification (ID) and measured data may be mutually exchanged by using a direction prediction index and the physical distance between the health or wellness service unit 1100 and the user terminal 1200 even without a user operation.

The user terminal 1200 performs bidirectional communication with the health or wellness service unit 1100, receives the biological signal measured from the health or wellness service unit 1100 and further transmits an ID unique to the user terminal 1200 and an received signal strength indication (RSSI) to the health or wellness service unit 1100.

In this case, the user terminal 1200 uses a terminal that may perform location-based wireless communication, such as a watch and glasses capable of implementing location-based wireless communication, in addition to a mobile terminal including a smart phone, a smart pad, an iPod, and a personal digital assistant (PDA), The operator server 1300 performs bidirectional communication between the health or wellness service unit 1100 and the user terminal 1200 through a network, analyzes finally measured data transmitted from the health or wellness service unit 1100 to manage health information on a subject, and provides requested health information for a user when there is a health information request from the user terminal 1200.

In this example, the finally measured data means data transmitted with a packet structure that includes information on a user ID, measured data (such as a blood pressure, blood sugar, and weight), a measured time, and a measuring device ID.

Although the network uses an IEEE 802.15.4 MAC, Bluetooth communication or Wi-Fi communication protocol in the present invention in order to construct a wireless sensor network, it may also apply variously depending on a technical development without limitation to the protocol above.

The configuration and function of the health or wellness service unit 1100 and the user terminal 1200 that form the important components of the present invention are described below in detail with reference to FIGS. 2A and 2B.

Figure 2A:
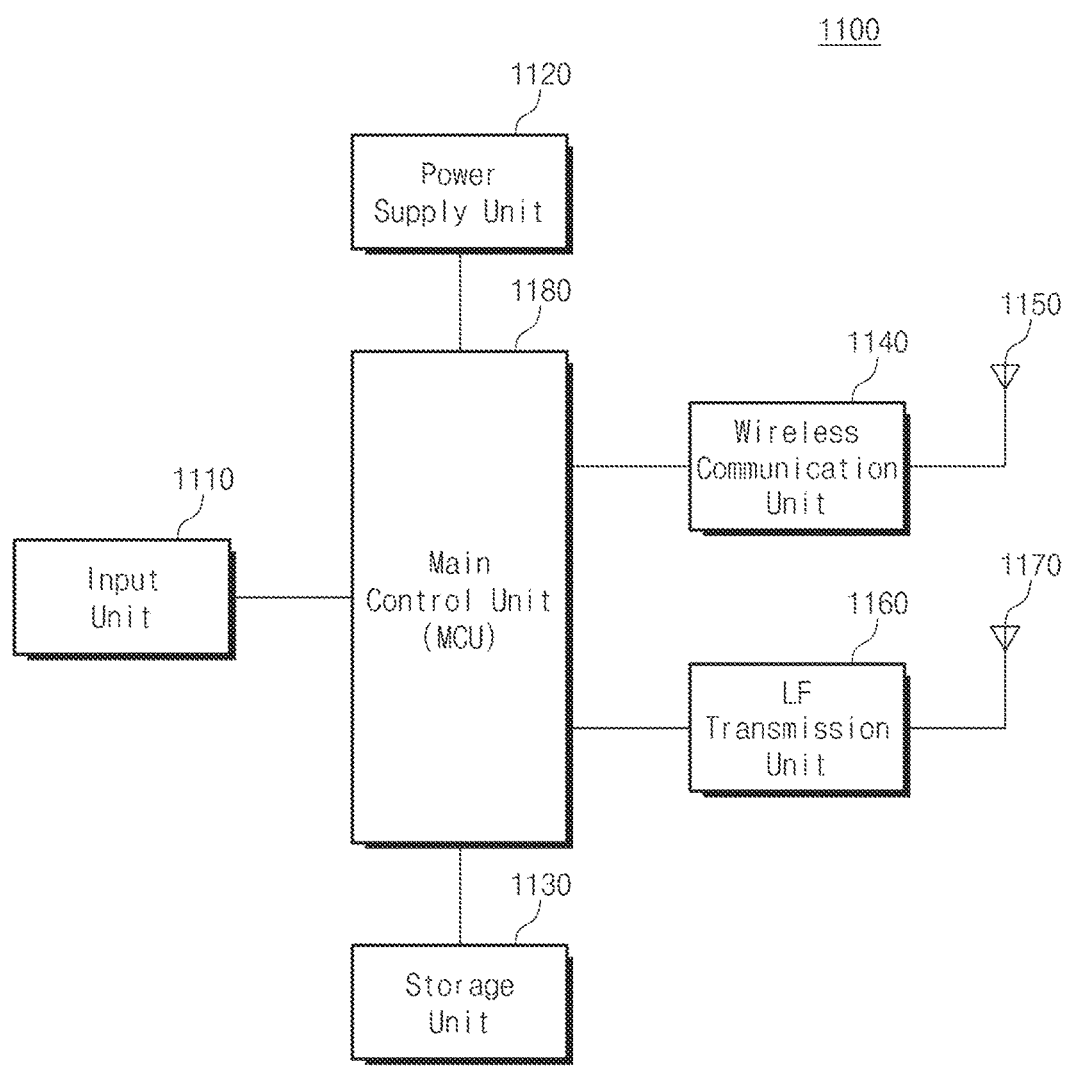
FIG. 2A specifies the configuration of a health or wellness service unit shown in FIG. 1.

FIG. 2A specifies the configuration of the health or wellness service unit shown in FIG. 1.

Referring to FIG. 2A, the health or wellness service unit 1100 of the present invention includes an input unit 1110, a power supply unit 1120, a storage unit 1130, a wireless communication unit 1140, a radio frequency (RF) antenna 1150, a low frequency (LF) transmission unit 1160, an LF antenna 1170, and a main control unit 1180.

The input unit 1110 is used for obtaining medial data on a subject and may use a button input type, a pen input type, and a touch input type.

The power supply unit 1120 plays a role of supplying power to the main control unit 1180, the wireless communication unit 1140, the RF antenna 1150, the LF transmission unit 1160, and the LF antenna 1170.

Medical data on a subject including various programs and measured biological signals needed for the operation of the main control unit 118 is stored in the storage unit 1130.

The wireless communication unit 1140 plays a role of processing a signal transmitted and received through the RF antenna 1150 and use a communication network such as an Ethernet, wireless broadband internet (WiBro), Wi-Fi, world interoperability for microwave access (WiMAX), high speed packet access (HSPA), code division multiple access (CDMA), or Bluetooth network.

The RF antenna 1150 transmits and receives a signal through RF communication with an external communication device and in this case, an IEEE 802.15.4 MAC, Blue tooth communication or Wi-Fi communication protocol may be used as a protocol of a network applied to wireless communication.

The LF transmission unit 1160 is used for transmitting data to an external user terminal 1200 and generates a wake-up signal waking up the user terminal 1200 for implementing low power and an LF signal for the location identification of the user terminal 1200.

The LF antenna 1170 transmits and receives a signal through LF communication with the external user terminal 1200 at a low frequency band of 10 kHz to 150 kHz.

The main control unit (MCU) 1180 controls the input unit 1110, the power supply unit 1120, the storage unit 1130, the wireless communication unit 1140, the RF antenna 1150, the LF transmission unit 1160, and the LF antenna 1170.

Figure 2B:
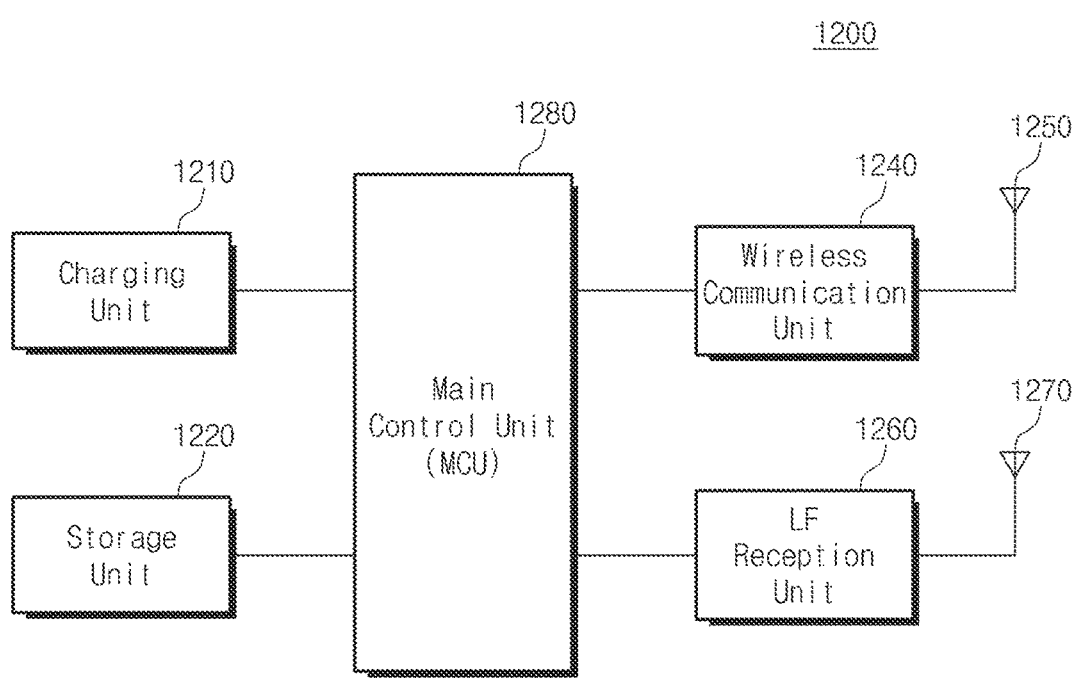
FIG. 2B specifies the configuration of a user terminal shown in FIG. 1.

FIG. 2B specifies the configuration of the user terminal shown in FIG. 1.

Referring to FIG. 2A, the user terminal 1200 of the present invention includes a charging unit 1210, a storage unit 1220, a wireless communication unit 1240, an RF antenna 1250, an LF reception unit 1260, an LF receiver antenna 1270 and a main control unit 1280.

The charging unit 1210 includes a battery to fill charges so that the user terminal 1200 may operate without a lack of charges.

Various programs needed for the operation of the main control unit 1280 and medical data transmitted from the health or wellness service unit 1100 are stored in the storage unit 1220.

The wireless communication unit 1240 plays a role of processing a signal transmitted and received through the RF antenna 1250 and may use a communication network such as an Ethernet, wireless broadband internet (WiBro), Wi-Fi, world interoperability for microwave access (WiMAX), high speed packet access (HSPA), code division multiple access (CDMA), or Bluetooth network.

The RF antenna 1250 transmits and receives a signal through RF communication with an external communication device and in this case, an IEEE 802.15.4 MAC, Blue tooth communication or Wi-Fi communication protocol may be used as a protocol of a network applied to wireless communication.

The LF transmission unit 1260 receives a wake-up signal for implementing low power transmitted by the external health or wellness service unit 1100 and an LF signal for the location identification of the user terminal 1200.

When the LF receiving unit 1260 senses an LF signal operating at lower power of several micrometers μm and generates certain wake-up interrupt in response to a sensed LF signal, the main control unit 1280 changes the wireless communication unit 1240 usually having a sleep state to a wake-up state, according to the interrupt.

In this case, the LF signal is transmitted at a frequency band of 10 kHz to 150 kHz, the distance between a signal transmitter and a signal receiver is 1 m to 10 m, and it is possible to identify the physical distance and direction between the health or wellness service unit 1100 and the user terminal 1200 3-dimensionally (x, y, z) by using the signal.

The LF reception unit 1260 measures an RSSI corresponding to a received signal when an LF signal for the 3-dimensional location identification of the user terminal 1200 from the health or wellness service unit 1100.

A measured RSSI is transmitted to the health or wellness service unit 1100 through the wireless communication unit 1240 according to the certain control of the main control unit 1280.

The LF receiver antenna 1270 transmits and receives a signal through LF communication with the external health or wellness service unit 1100.

The main control unit (MCU) 1280 controls the charging unit 1210, the storage unit 1220, the wireless communication unit 1240, the RF antenna 1250, the LF reception unit 1260, and the LF receiver antenna 1270.

FIG. 3 represents the sequence diagram of a protocol for providing a health care service between the body index measuring unit and the user terminal of the present invention.

A method of providing the health care service between a plurality of user terminals 1200*a* and 1200*b* and the health or wellness service unit 1100 of the present invention is described with reference to FIG. 3.

First, when first and second user terminals 1200*a* and 1200*b* are turned on and are adjacent to each other, the health or wellness service unit 1100 transmit wake-up signals to the first user terminal 1200*a* and the second user terminal 1200*b*, respectively in steps a10 and b10.

Next, the first and second user terminals 1200*a* and 1200*b* sense wake-up signals through each LF receiver 1260, then generate certain interrupt and change each state from an usual sleep state to an wake-up state in steps a20 and b20.

Next, when a service event occurs, the health or wellness service unit 1100 transmits a corresponding service advertising message to the first and second user terminals 1200*a* and 1200*b* in steps a40 and b40.

In this example, the service event means a case where there is a service advertising message to be provided for a user.

Next, the first and second user terminals 1200*a* and 1200*b* transmit IDs unique to each of the terminals, RSSI and received-signal direction information to the health or wellness service unit 1100 in steps a50 and b50.

Next, the health or wellness service unit 1100 compares RSSI values and received-signal direction values transmitted from the first and second user terminals 1200*a* and 1200*b*, comprehensively analyzes the physical distances between the user terminals and the health or wellness service unit and the states of the user terminals and selects a user terminal satisfying an optimal communication state.

As an example, when a first RSSI value transmitted from the first user terminal 1200*a* is larger than a second RSSI value transmitted from the second user terminal 1200*b* and other communication states are the same, the health or wellness service unit 1100 selects the first user terminal 1200*a*.

Next, the health or wellness service unit 1100 transmits measured data to a selected first user terminal 1200*a* in step a70.

Lastly, the first user terminal 1200*a* checks a response message informing that measured data is received in step a80, and the second user terminal 1200*b* checks a response message informing that measured data is not received in step b80.

Figure 4A:
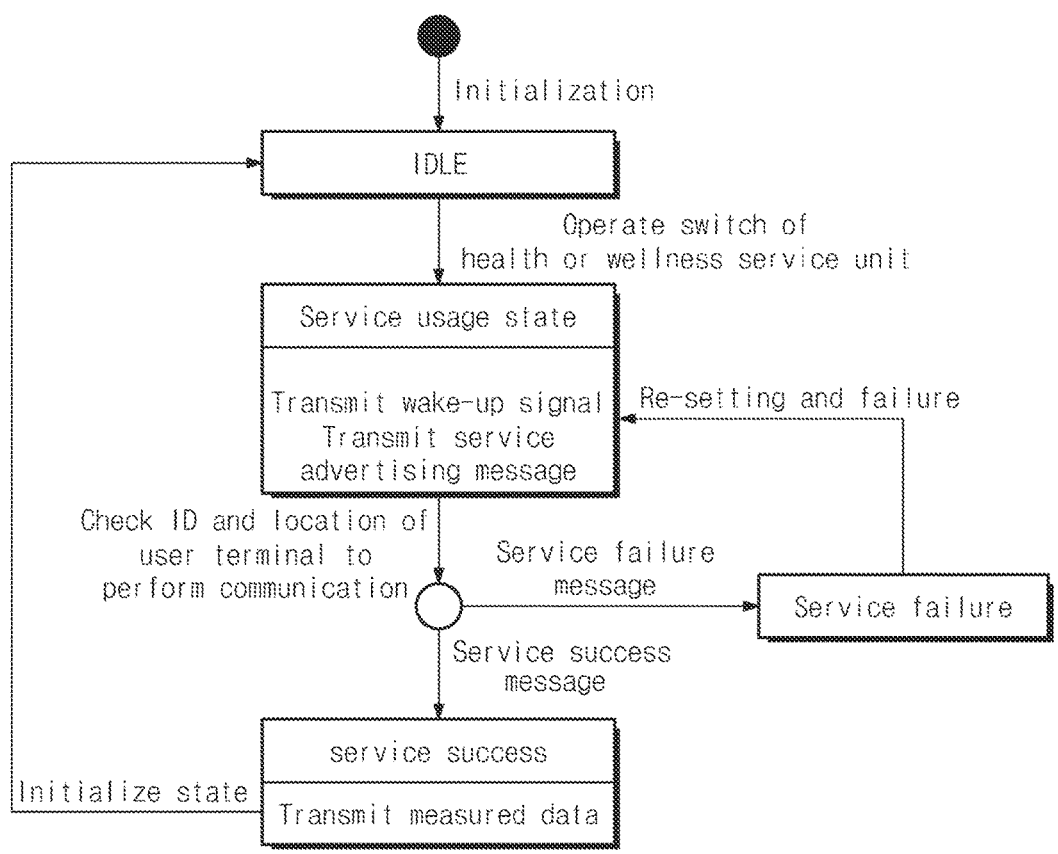
FIG. 4A represents a state diagram related to the operation of the health or wellness service unit of the sequence diagram of the protocol of FIG. 3.
Figure 4B:
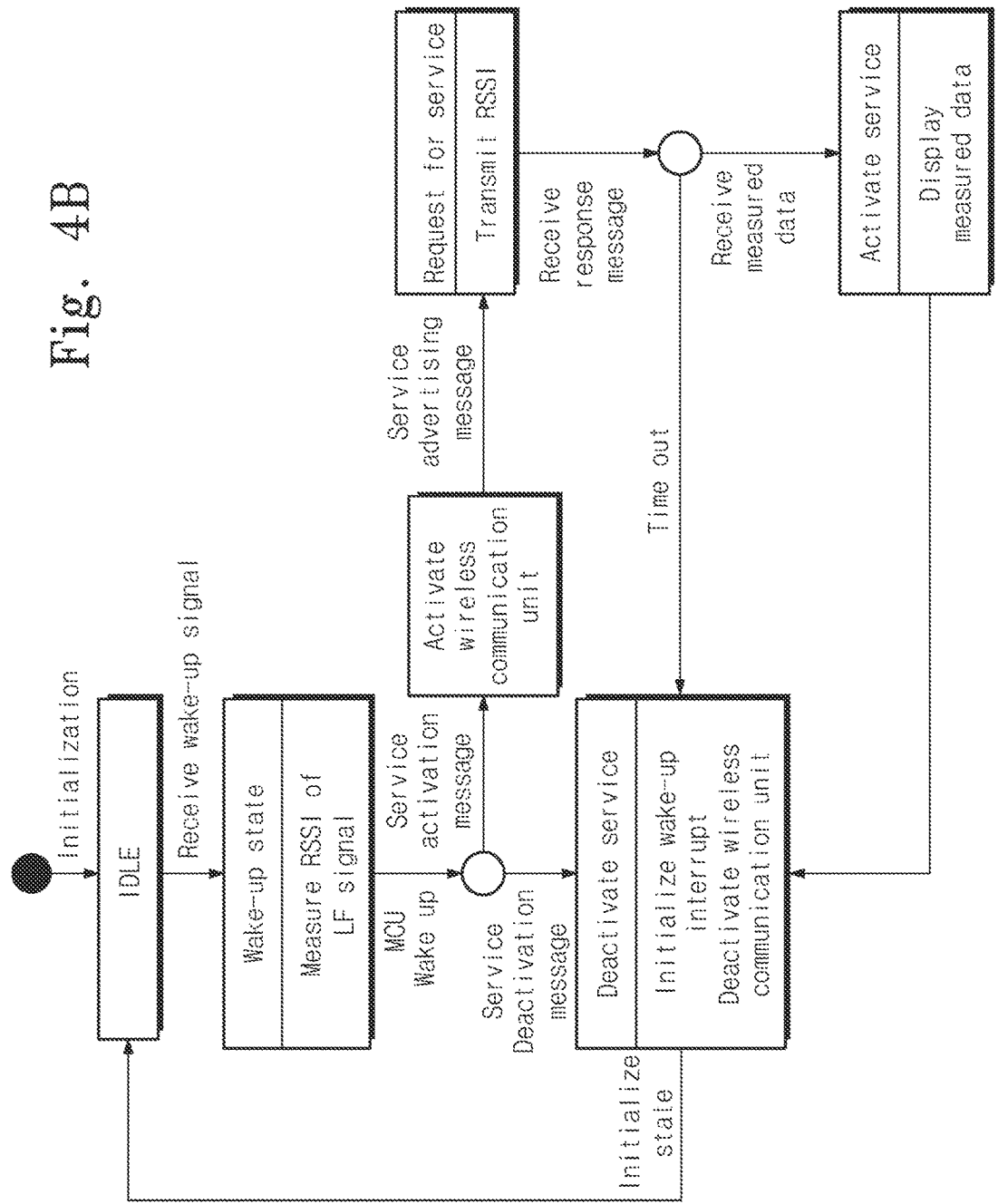
FIG. 4B represents a state diagram related to the operation of the user terminal of the sequence diagram of the protocol of FIG. 3.

The execution state of each step of FIG. 3 is described in detail based on the operation states of the health or wellness service unit and the user terminals with reference to FIGS. 4*a* and 4*b*.

FIG. 4A represents a state diagram related to the operation of the health or wellness service unit of the sequence diagram of the protocol of FIG. 3.

Referring to FIG. 4A, when an observer presses the start switch of the health or wellness service unit 1100 in order to measure physical indexes such as a blood pressure and weight of a subject, the health or wellness service unit changes from an initial IDLE state to a service usage state.

In the service usage state, the health or wellness service unit 1100 transmits a wake-up signal and a service advertising message to the user terminal 1200.

The health or wellness service unit 1100 receives an ID unique to a terminal and an RSSI from the user terminal 1200 and checks the ID and location of the user terminal 1200.

When a service request signal is received from the user terminal 1200, the health or wellness service unit 1100 changes to a service success state and transmits requested, measured data to the user terminal 1200.

When communication is not made with the user terminal 1200, the health or wellness service unit 1100 changes to a service failure state, transmits a service failure message to the user terminal 1200, and changes to an IDLE state through initialization.

FIG. 4B represents a state diagram related to the operation of the user terminal of the sequence diagram of the protocol of FIG. 3.

Referring to FIG. 4B, when the user terminal 1200 receives a wake-up signal and an LF signal of a LF band from the health or wellness service unit 1100, the user terminal 1200 generates wake-up interrupt in response to a sensed wake-up signal and changes from an usual sleep state to a wake-up state.

In the wake-up state, the user terminal 1200 measures an RSSI corresponding to a received LF signal and enables it to be used for location sensing.

The main control unit MCU 1280 that is in a wake-up state checks whether a service is activated, and when the service is in an inactive state, the MCU initializes wake-up interrupt and inactivates the wireless communication unit 1240 to set back to an initial IDLE state.

On the contrary, when the MCU 1280 checks whether a service is in an active state and if positive, the MCU changes the wireless communication unit 1240 to the active state to be able to receive a service advertisement message from the health or wellness service unit 1100, after which the user terminal 1200 changes to a service request state.

In the service request state, the user terminal 1200 transmits an RSSI corresponding to an LF signal and an ID unique to a terminal to the health or wellness service unit 1100.

When a response message received from the health or wellness service unit 1100 includes measured data, the user terminal 1200 changes to a service activation state and displays measured data.

On the contrary, when a response message received from the health or wellness service unit 1100 does not include measured data or there is no response for a preset time period, such as in a time-out situation, the user terminal 1200 changes to a service inactivation state to initialize wake-up interrupt and inactivates the wireless communication unit 1240 to set back to an initial IDLE state.

In the following, a user activity pattern management system according to an embodiment of the present invention is described. The user activity pattern management system according to an embodiment of the present invention includes terminals installed at devices provided for a user activity area and a portable terminal that receives activity data from a terminal according to a user's usage action to the device, and collects user activity pattern data. The terminal senses that user's device usage and transmits a wake-up signal to a portable terminal, and the portable terminal changes from a sleep mode to a wake-up mode according to a wake-up signal and receives activity data directly from the terminal by using proximity-based neighbor device wake-up and automatic user identification function.

According to the user activity pattern management system according to an embodiment of the present invention, it is possible to identify a user activity pattern by only performing an ordinary activity without a need for a user to perform a complex operation on a portable terminal. Also, since the portable terminal does not always operate in order to monitor a user's ordinary activity but only when a user uses a device, the portable terminal wakes up so that user activity pattern data may be obtained, it is possible to minimize the power consumption of the portable terminal and the terminal installed at the device and it is possible to extend a battery charging cycle or replacing cycle and thus enable long-term use.

The user activity pattern management system according to an embodiment of the present invention may include activity data, a portable terminal's ID and device usage time information in one data packet to collect user activity pattern data. The portable terminal's ID 1:1 corresponds to a user ID and it may be said that the portable terminal's ID represents the user ID. The user activity pattern data formed as a single data packet may be transmitted to the personal mobile terminal of a user or a guardian or an external device such as a hospital server and it is possible to comprehensively check user activity pattern data on a user through a corresponding external device.

In an embodiment of the present invention, the portable terminal may provide a notification function at a time corresponding to each schedule on a schedule management list according to a preset schedule management list, and generate an alarm signal or transmit an alarm message to an external device when the schedule management list does not match user activity pattern data or an abnormal activity pattern is sensed. According to an embodiment of the present invention, it is possible to help a user to perform an ordinary activity according to the schedule management list, and when a user does not act according to the schedule management list, it is possible to generate an alarm and provide a notice for a user or transmit an alarm message to an external device. Accordingly, it is possible to manage a user activity pattern by providing a notice for a guardian or a medical specialist.

In an embodiment of the present invention, the portable terminal may generate a wake-up event at a time corresponding to each schedule of the schedule management list, changes to a wake-up mode according to the wake-up event, and transmit a control message to a terminal of a device side corresponding to each schedule of the schedule management list, the terminal installed at a device may receive a control message, sense the approach or the portable terminal, communicates with the control unit of the device and automatically operate the device according to the control message. According to an embodiment of the present invention, since a device may automatically operate as scheduled only by an action that a user carrying a portable terminal approaches the device corresponding to a schedule on a schedule management list, it is possible to perform an activity as scheduled by using a device even if it is complicated to operate the device.

In an embodiment of the present invention, a guardian or a medical specialist may transmit an SMS command message to a user's mobile terminal by using a mobile terminal, the user's mobile terminal may check a meta script of the SMS command message and transmit a control command signal corresponding to a command to a portable terminal, and the portable terminal may modify a schedule management list according to the control command signal, transmit a control message for automatically operating a device to a terminal of the device or transmit user activity pattern data to a user's or guardian's mobile terminal or a hospital server. According to an embodiment of the present invention, a user's guardian or a medical specialist may remotely manage a user activity pattern though a mobile terminal or outside the hospital.

Figure 5:
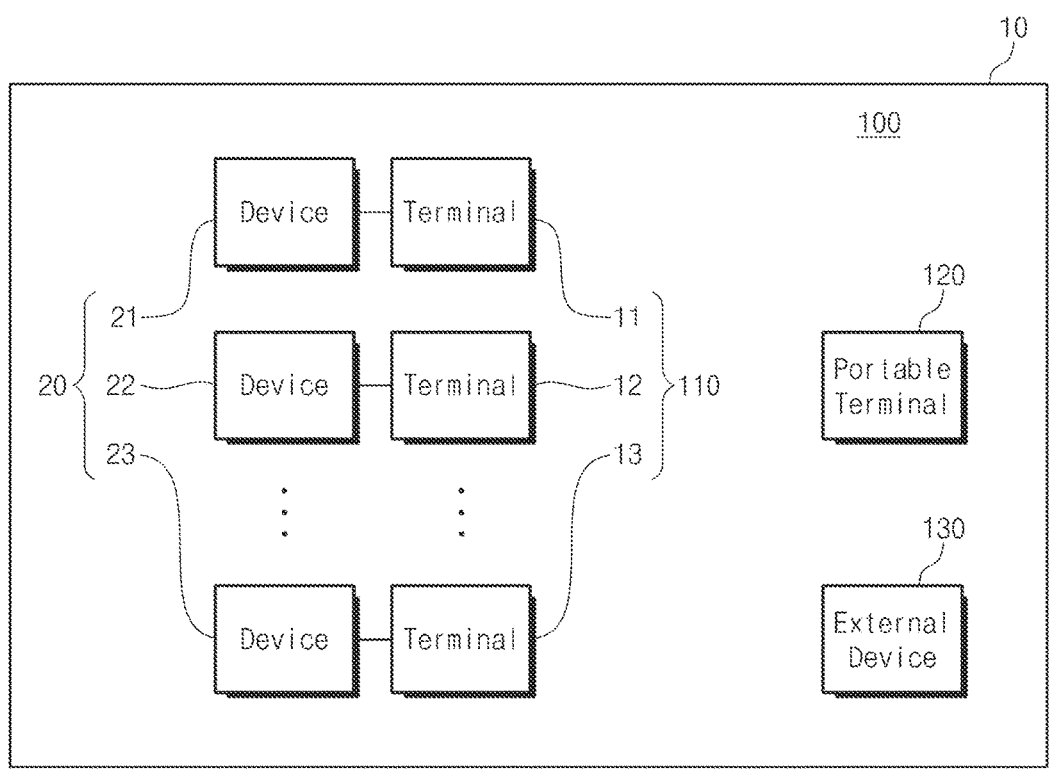
FIG. 5 is a schematic diagram of a user activity pattern management system according to an embodiment of the present invention.

FIG. 5 is a schematic diagram of a user activity pattern management system according to an embodiment of the present invention; Referring to FIG. 5, a user activity pattern management system 100 according to an embodiment of the present invention includes a plurality of terminals 110, a portable terminal 120, and an external device 130. Terminals 11 to 13 are installed at devices 21 to 23 that are provided in a user activity area 10.

The activity area 10 may be a space such as a user's residential space, office or fitness center. For example, when the activity area 10 is a residential area, the device 20 may be devices needed for daily life, such as a refrigerator, a toilet bowl, a medicine storage drawer, a microwave oven, a gas range, a TV, a phone or a water purifier. As another example, when the activity area 10 is a fitness center, the device may be sports equipment such as a treadmill, a cycle or a bench press.

Terminals 11 to 13 may be installed on the external surfaces of or inside corresponding devices 21 to 23 or may also be installed at locations adjacent to corresponding devices 21 to 23. The terminal 110 includes a sensor 111 (of FIG. 8) that senses whether a user uses the device 20. When a user carrying the portable terminal 120 uses the device 20, the terminal 110 senses that the user uses the device and then transmits a wake-up signal to the portable terminal 120.

The portable terminal 120 changes from a sleep mode to a wake-up mode according to the wake-up signal and receives activity data directly from the terminal by using proximity-based neighbor device wake-up and automatic user identification function. The portable terminal 120 receives activity data from the terminals 11 to 13 according to a user's usage action to the device 20 and collects user activity pattern data. The portable terminal 120 may be a wearable terminal that is provided with a small size and light weight so that a user may wear and carry it.

Figure 6:
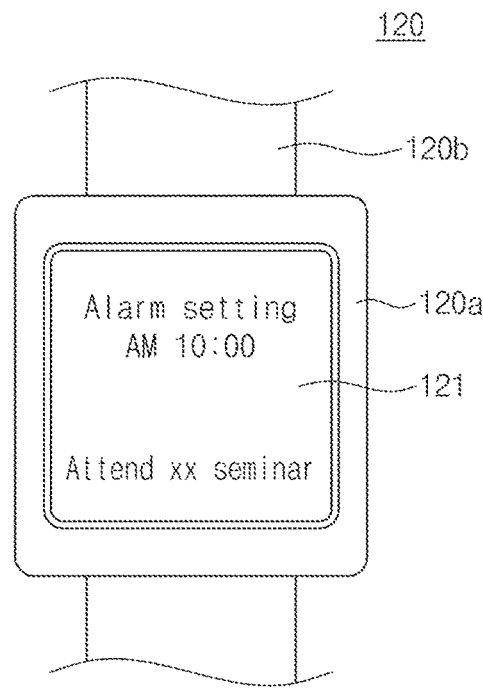
FIG. 6 shows a portable terminal configuring a user activity pattern management system according to an embodiment of the present invention.

FIG. 6 shows a portable terminal configuring a user activity pattern management system according to an embodiment of the present invention. As in an embodiment shown in FIG. 6, the portable terminal 120 may be provided with a form similar to a general wrist watch that includes a housing 120a that has a display unit 121, and a watch strap 120b that is connected to both sides of the housing. However, the form of the portable terminal is not limited to that shown in FIG. 6

Figure 7A:
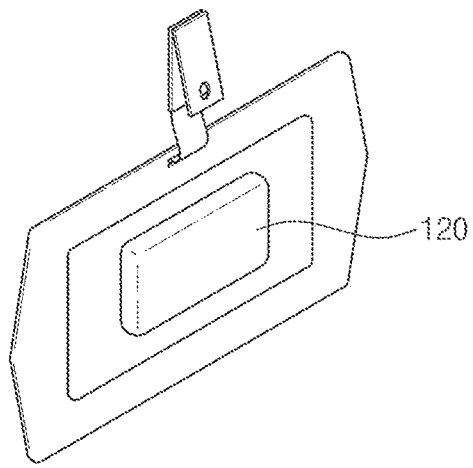
FIGS. 7A to 7C show a portable terminal configuring a user activity pattern management system according to an embodiment of the present invention.
Figure 7B:
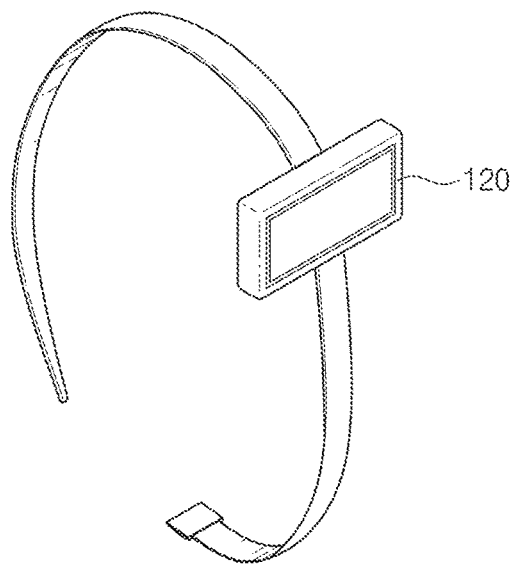
Figure 7C:
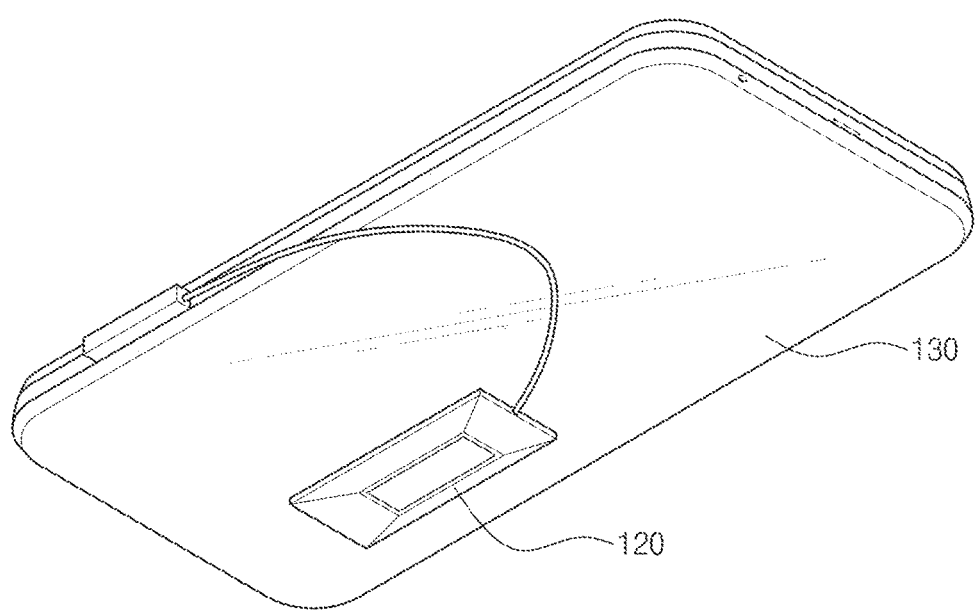

FIGS. 7A to 7C show a portable terminal configuring a user activity pattern management system according to another embodiment of the present invention. The portable terminal 120 may be provided e.g., a pass form as shown in FIG. 7A, installed on glasses, clothing or belt as shown in FIG. 7B, or installed at an external device 130 such as a mobile phone as shown in FIG. 7C.

Referring back to FIG. 5, the portable terminal 120 may perform short-range communication with the terminal 110 through LF transmission and reception, change from a sleep mode to a wake-up mode according to a wake-up signal received from the terminal 110, and receive activity data corresponding to a usage action from the terminal 110. As an embodiment, activity data may include a terminal ID, a device ID, and the ON/OFF operation of a device.

The portable terminal 120 may use activity data received from the terminal 110 to collect user activity pattern data. As an embodiment, the user activity pattern data may include activity data, a portable terminal ID and usage time information. The portable terminal 120 may include portable terminal 120 ID, activity data and device operation time information corresponding to activity data in one data packet to collect the user activity pattern data.

The external device 130 may be a user's or guardian's personal mobile terminal such as a smart phone. The external device 130 may operate in linkage with the portable terminal 120. For example, the external device may collect user activity pattern data from the portable terminal 120 to store or display it on a screen. As another example, the external device 130 may transmit a control command signal that includes a command to transmit a schedule management list to the portable terminal 120, automatically operate the device 20 or request the transmission of user activity pattern data or modify the schedule management list.

The external device 130 may use wireless communication functions such as WiFi and Bluetooth to transmit user activity pattern data or an alarm message to an external mobile terminal of a guardian located outside the activity area 10 or a hospital server or receive an SMS command message therefrom and the control command signal to the portable terminal 120. When there is no external device 130 in the activity area 10, the portable terminal 120 may transmit and receive information to an external mobile terminal of a guardian outside the activity area 10 or a hospital server.

As an embodiment, the portable terminal 120 may provide an alarm function at a time corresponding to each schedule on a schedule management list according to a preset schedule management list. The portable terminal 120 checks whether the schedule management list matches the user activity pattern data and when the schedule management list does not match the user activity pattern data or an abnormal activity is sensed through the activity pattern data, it is possible to generate an alarm signal or transmit an alarm message to an external device 130 located in the activity area 10 or a hospital server or a mobile terminal of a guardian located outside the activity area 10.

Figure 8:
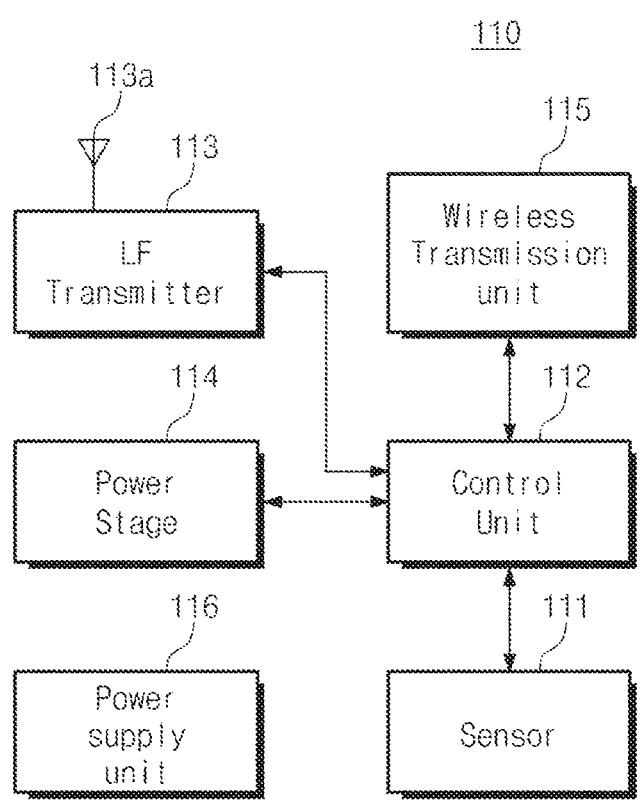
FIG. 8 is a schematic diagram of a terminal configuring a user activity pattern management system according to an embodiment of the present invention.

FIG. 8 is a schematic diagram of a terminal configuring a user activity pattern management system according to an embodiment of the present invention. Referring to FIGS. 5 and 8, the terminal 110 includes a sensor 111, a control unit 112, an LF transmitter 113, a power stage 114, a wireless transceiving unit 115, and a power supply unit 116. The control unit 112 controls various functions of the sensor 111, the LF transmitter 113, the power stage 114, and the wireless transceiving unit 115. As an embodiment, different terminals 11 to 13 may also include the same sensors 111 or different types of sensors 111.

When a user carrying the portable terminal 120 uses the device 20, the sensor 111 senses user's usage action to a corresponding device 21, 22 or 23. The sensor 111 may be e.g., a hall sensor, a touch sensor such as a piezo sensor, a loadcell, a photo sensor, a thermal sensor, an angular sensor or an ammeter. For example, in the case of a refrigerator or a medicine storage drawer, it is possible to a user's usage action by installing a touch sensor on a knob, and in the case of a TV or a microwave oven, it is possible to sense a home appliance usage action by installing an ammeter. For example, when using the ammeter, it is possible to sense a usage action by checking a current flowing through a power supply when the terminal 110 operates with a constant power supply, and when there is no constant power supply, it is possible to attach a battery tag and sense a usage action by checking a current flowing through a tag in operation.

The terminal 1110 is maintained in a low power standby mode when sensing a user's usage action, and does not attempt to communicate with the portable terminal 120 in this case. If the sensor 111 senses a user's usage action, the terminal 110 attempts to communicate with the portable terminal 120. As the sensor 111 senses the user's usage action, the LF transmitter 113 transmits a wake-up signal to the portable terminal 120 through the transmission antenna 113a. The LF transmitter 113 uses a low-power LF signal having an LF band such as 10 to 150 KHz to perform short-range communication with the portable terminal 120.

When there is a plurality of users individually carrying and using the portable terminal 120 near the device 20 in the activity area 10, the terminal 110 may use a low-power LF signal to predict the distance of the portable terminal 120 wore by adjacent users by using a low-power LF signal, and select the most suitable portable terminal 120, which is estimated as using the device 20, based on the distance.

The power stage 114 sets the terminal 110 to a low-power standby mode until the sensor 111 senses a user's usage action, and when the sensor 111 senses the user's usage action, the power stage raises power and operates the LF transmitter 113. When activity data is transmitted from the terminal 110 to the portable terminal 120, the power stage 114 again operates the terminal 110 in a low-power standby mode until a new usage action is sensed.

The wireless transceiving unit 115 may transmit activity data corresponding to a usage action to the portable terminal 120 through radio frequency (RF) communication, and receive a control message from the portable terminal 120. The wireless transceiving unit 115 may communication with the portable terminal 120 by using e.g., a Bluetooth or WiFi scheme.

The power supply unit 116 supply direct current (DC) or alternating current (AC) power to the terminal 110. The power supply unit 116 may be provided as a 220 V constant power supply that is used for general home, or include a small battery when a constant power supply is not used. When the terminal 110 is installed in the device 20, the power supply unit 116 may receive some of power supplied to the device 20 through a socket from the device 20 and supply power to the terminal 110. Alternatively, the power supply unit 116 may be provided in a chargeable or replaceable battery type and also supply power to the terminal 110.

Figure 9:
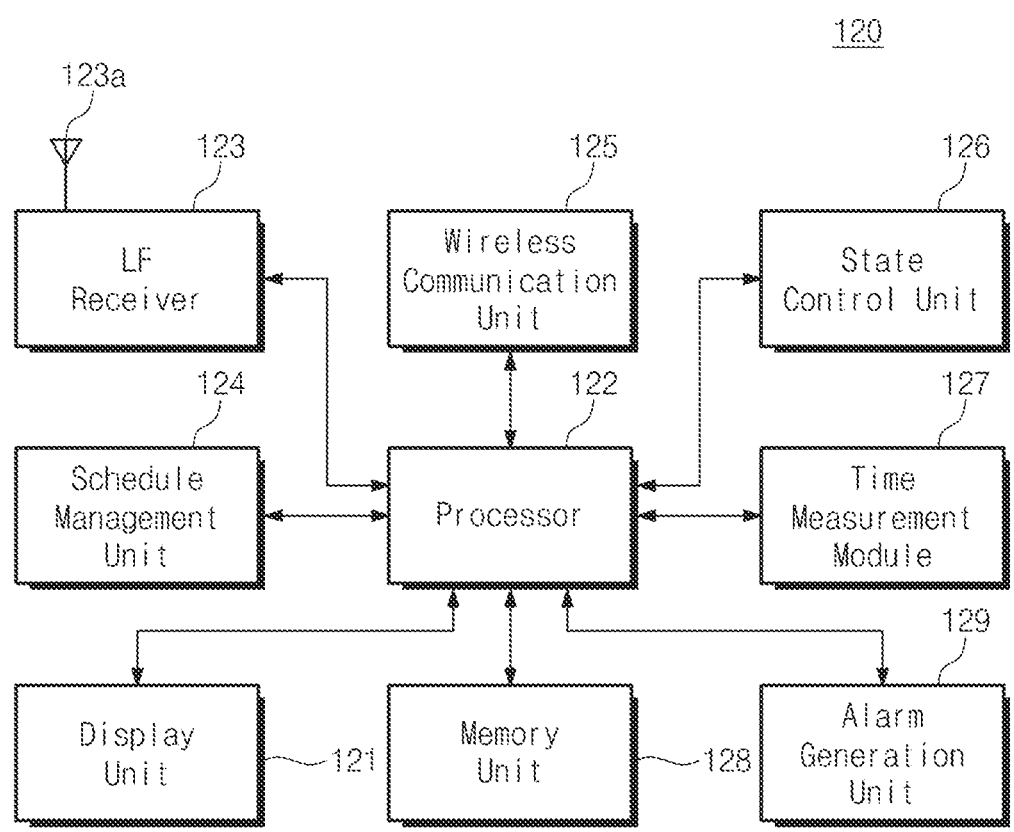
FIG. 9 is a schematic diagram of a portable terminal configuring a user activity pattern management system according to an embodiment of the present invention.

FIG. 9 is a schematic diagram of a portable terminal configuring a user activity pattern management system according to an embodiment of the present invention. Referring to FIG. 9, the portable terminal 120 includes a display unit 121, a processor 122, an LF receiver 123, a schedule management unit 124, a wireless communication unit 125, a state control unit 126, a time measurement module 127 measuring time information, a memory unit 128, and an alarm generation unit 129. The processor 122 controls various functions of the display unit 121, the LF receiver 123, the schedule management unit 124, the wireless communication unit 125, the state control unit 126, the time measurement module 127, the memory unit 128, and the alarm generation unit 129.

The display unit 121 may display the current date and time through an LCD screen similarly to the fundamental operation of a general wrist watch. As an embodiment, the display unit 121 may display the details of a corresponding schedule at a time corresponding to each schedule in order to provide the schedules of a schedule management list for a user.

The portable terminal 120 is maintained in a sleep mode until receiving a wake-up signal from the terminal 110, and does not attempt to communicate with the terminal except when transmitting a control message.

If the wake-up signal is received from the terminal 110, the portable terminal 120 changes from a sleep mode to a wake-up mode according to a received wake-up signal, communicates with the terminal 110, and receives activity data corresponding to a usage action from the terminal 110.

Figure 11:
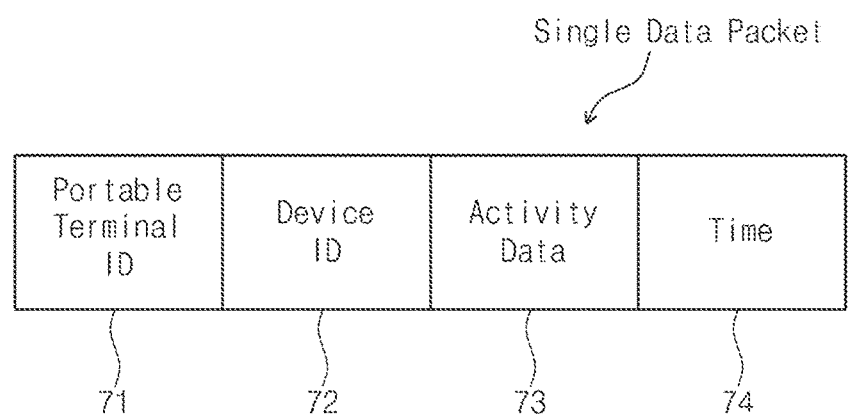
FIG. 11 shows a single data packet stored in a portable terminal configuring a user activity pattern management system according to an embodiment of the present invention.

The LF receiver 123 receives the wake-up signal from the terminal 110 through the reception antenna 123a. Like the LF transmitter 113, the LF receiver 123 may perform LF communication such as short-range communication of several centimeters to several dozens of centimeters through a 100 KHz to 130 KHz band. The portable terminal 120 receives activity data from the terminal 110 and may then change from the wake-up mode back to the sleep mode. The processor 122 may use activity data received from the terminal 110 to collect user activity pattern data. As an embodiment, the user activity pattern data may include activity data, an portable terminal ID and usage time information. As shown in FIG. 11, the processor 122 may include an ID 71 of the portable terminal 120, an ID 72 of the device 20, activity data 73 and operation time information 74 on a device corresponding to activity data in one data packet to collect user activity pattern data.

Figure 10:
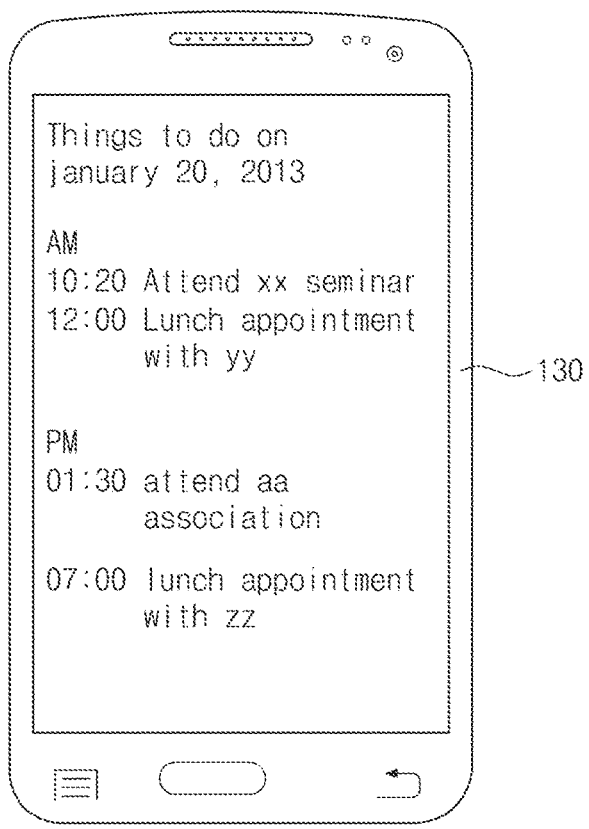
FIG. 10 shows an external device configuring a user activity pattern management system according to an embodiment of the present invention.

Referring back to FIG. 9, the schedule management unit 124 may provide an alarm function at a time corresponding to each schedule on a schedule management list according to a preset schedule management list. FIG. 10 shows an external device configuring a user activity pattern management system according to an embodiment of the present invention. Referring to FIG. 10, the external device 130 includes a schedule management application that may set or change a schedule management list through a user interface. The schedule management list set by the external device 130 is transmitted to the portable terminal 120. The schedule management unit 124 may display the details of a schedule on e.g., the display unit 121 as shown in FIG. 6 or additionally generate a sound or vibration providing the details of the schedule through the alarm generation unit 129 to provide the schedule for a user. The schedule management unit 124 may also update the schedule management list according to a schedule management message from the external device 130. A time corresponding to each schedule may be set as the start time of a corresponding schedule, before a certain hour therefrom, or a preset time.

The schedule management unit 124 may receive a schedule management message from the external device 130 and update the schedule management list according to the schedule management message. For example, when a user or guardian executes a schedule management application of the personal mobile terminal of a user or guardian, wireless communication is automatically established between the portable terminals, and when the schedule management list is updated through the application, the application transmits update information to the portable terminal 120. Then, the portable terminal 120 may reflect received update information to the current schedule management list, provide a notification function to a user according to an updated schedule management list and help with user's daily life.

In an embodiment of the present invention, the schedule management unit 124 may check whether user activity pattern data matches a schedule management list, and when negative, the schedule management unit may generate an alarm signal through the alarm generation unit 129 or transmit an alarm message to the mobile terminal of a guardian or a hospital server. For example, it is assumed that the schedule management list includes a medicine taking schedule. In this case, when a user opens a medicine storage drawer and takes a medicine at a time set for a corresponding medicine taking schedule, activity data is transmitted from the terminal 110 to the portable terminal 120 and the portable terminal 120 collects user activity pattern data representing when the user has taken a medicine.

When a medicine taking schedule has been provided but a user has not taken a medicine at a time set as a medicine taking schedule for some reasons such as forgetting, activity data is not transmitted from the terminal 110 to the portable terminal 120 since the sensor 111 installed at the medicine storage drawer senses a usage action. Thus, the medicine taking schedule will be left out from user activity pattern data on the portable terminal 120. In such a case, the schedule management unit 124 may determine that a schedule management list does not user activity pattern data, generate an alarm signal through the alarm generation unit 129, and transmit an alarm message to the mobile terminal of a guardian or a hospital server to provide a notice that a user such as a patient has not taken a medicine, for the guardian or a medical specialist.

The wireless communication unit 125 may receive activity data from the terminal 110 through RF communication. For example, the wireless communication unit 125 may broadcast request data including an ID of the portable terminal 120 in a wake-up mode according to a wake-up signal from the terminal 110. Accordingly, the wireless transceiving unit 115 of the terminal 110 may transmit activity data to the portable terminal 120 in response to the request data from the portable terminal 120.

The wireless communication unit 125 may transmit a control message from the terminal 110, transmit user activity pattern data to the external device 130 or receive a control command signal or a schedule management message from the external device 130. The wireless communication unit 125 may communicate with the terminal 110 and the external device 130 by using e.g., a Bluetooth or WiFi scheme.

The state control unit 126 may activate or inactivate the wireless communication function of the wireless communication unit 125 in e.g., a preset cycle. The processor 122 may broadcast a reception request message through the wireless communication unit 125 while a wireless communication function is activated by the state control unit 126. The external device 130 may transmit an acknowledgement message to the portable terminal 120 in response to the reception request message.

The processor 122 sets a wireless network in response to the acknowledgement message and transmits user activity pattern data to the external device 130 on a single data packet basis. When a wireless communication function is inactivated or the wireless communication function is activated but the acknowledgement message corresponding to the reception request message is not transmitted from the external device 130, the processor 122 may store user activity pattern data in the memory unit 129 and transmit accumulated user activity pattern data to the external device 130 when a wireless network is set.

Figure 12:
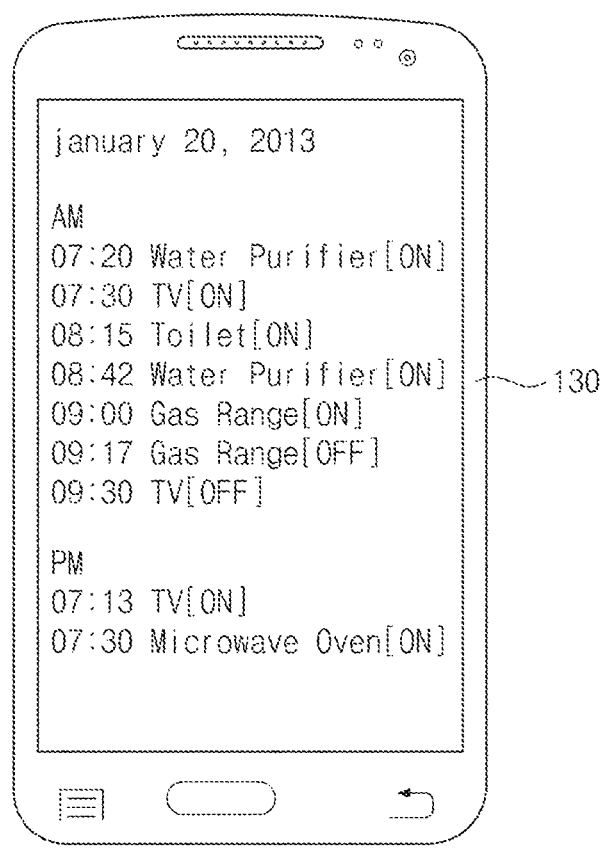
FIG. 12 shows an external device configuring a user activity pattern management system according to an embodiment of the present invention.

FIG. 12 shows an external device configuring a user activity pattern management system according to an embodiment of the present invention. Referring to FIG. 12, the external device 130 may display user activity pattern data transmitted from the portable terminal 120 on a display screen. An embodiment shown in FIG. 12 represents an example of when user activity pattern data is transmitted to the mobile terminal of a user or guardian, but another external device such as a hospital server may also receive the user activity pattern data.

Referring back to FIG. 9, the schedule management unit 124 may generate a wake-up event at a time set for each schedule on a schedule management list. The portable terminal 120 changes to a wake-up mode according to a wake-up event and transmits a control message to the terminal 110 of a device 20 side corresponding to each schedule. To this end, the portable terminal 120 may further include an LF transmitter in addition to the LF receiver 123.

Figure 13:
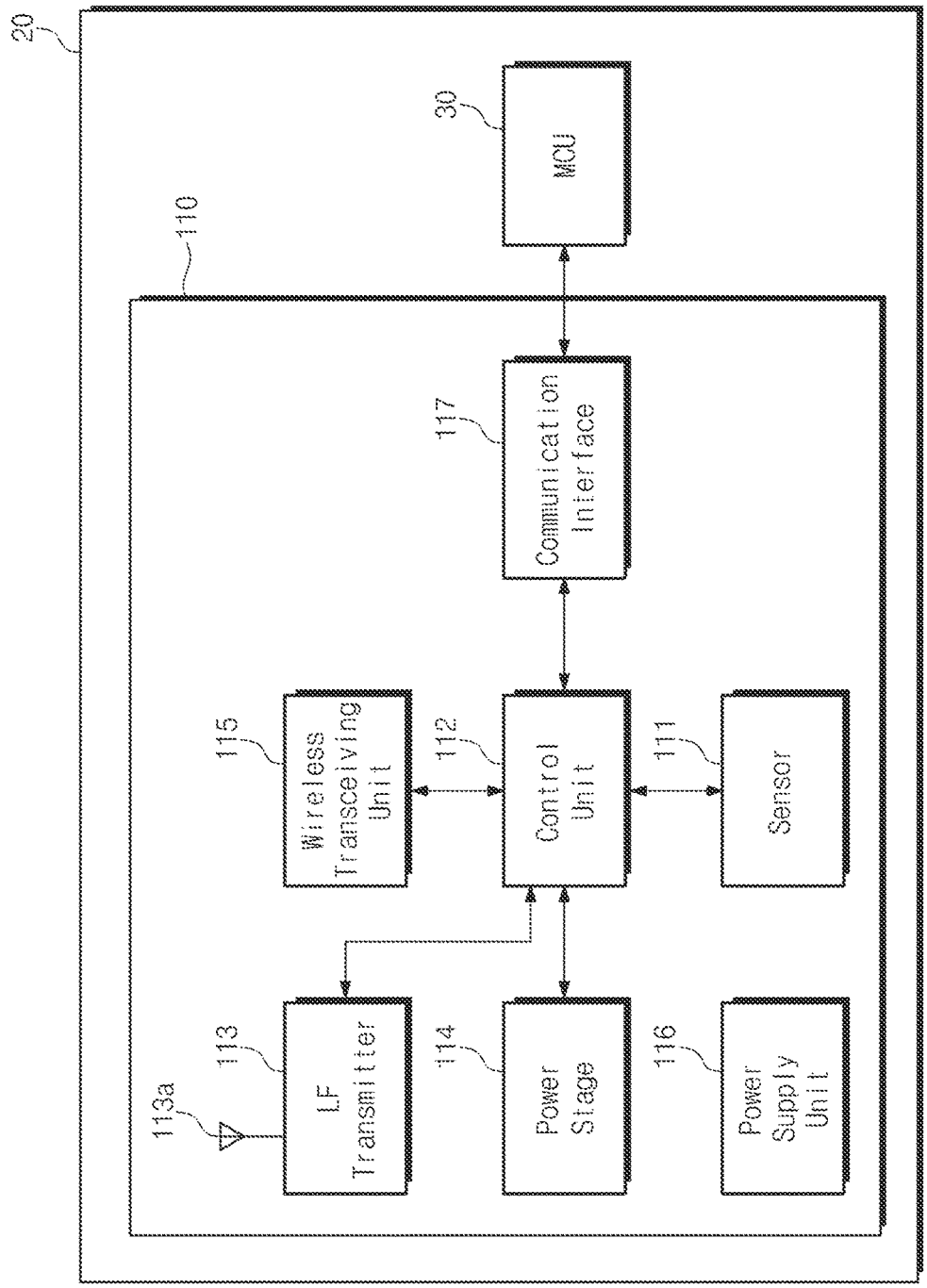
FIG. 13 is a schematic diagram of a terminal configuring a user activity pattern management system according to another embodiment of the present invention.

FIG. 13 is a schematic diagram of a terminal configuring a user activity pattern management system according to another embodiment of the present invention. When describing an embodiment shown in FIG. 13, components described in the embodiment shown in FIG. 8 are not described. The terminal 110 is installed in the device 20 and includes a communication interface that communicates with the control unit 30 of the device 20. The terminal 110 may receive a control message from the portable terminal 120, sense the approach of the portable terminal 120 and communicate with the control unit 30 of the device 20 through a communication interface 117 to automatically operate the device 20 according to the control message. The terminal 110 may communicate with the control unit 30 of the device 20 by using a serial communication scheme such as a universal asynchronous receiver/transmitter (UART), an inter-integrated circuit bus (I2C) or a serial peripheral interface (SPI), for example.

According to an embodiment of the present invention, if a user checks notification information provided according to a schedule management list by the portable terminal 120 and simply approaches the device 20 side according to a corresponding schedule, the operation of the device 20 is automatically performed according to a control message transmitted through wireless communication. Thus, it is possible to provide convenience for users who have difficulties in operating the device 20.

Referring back to FIG. 5, the external device 130 may receive an SMS command message from an external mobile terminal (not shown), read the SMS command message and transmit a corresponding control command signal to the portable terminal 120. The portable terminal 120 may modify a schedule management list, transmit a control message for automatically operating the device 20 to the terminal 110, or transmit user activity pattern data to the external device 130 or the external mobile terminal, according to a control command signal.

According to an embodiment of the present invention, only with a daily activity that a user simply does a job or opens the door of a refrigerator in order to take food out even if a user such as a patient does not perform a separate operation on the terminal 110 or the portable terminal 120, activity information is integrated with user information and an activity time to be collected as activity pattern data. Since user activity pattern data is compared with a schedule management list provided from a personal mobile terminal by the portable terminal 120 and a comparison result is transmitted to a guardian or family doctor in real time or regularly, the guardian or the family doctor may identify and analyze the activity pattern of patients living in a remote space and may quickly cope with an emergency situation.

The user activity pattern management system 100 according to an embodiment of the present invention may help a user that needs regular management such as personal health care management or medical data measurement or ordinary people that have important schedules or works. If the user activity pattern management system 100 according to an embodiment of the present invention is applied to a fitness center, a user may see with which sports equipment or how long he or she has exercised, through a smart phone, only with the operation of executing the schedule management application of the smart phone without a special operation.

If an exercise time for individual sports equipment is set by using a schedule management application of a smart phone and stored as a schedule management list, it is possible to use various pieces of sports equipment according to a schedule set through the notification function of the portable terminal 120, so it is possible to maximize an exercise effect. Also, when user activity pattern data does not match an exercise schedule, it is possible to provide corresponding information for a trainer in order to raise user activity pattern data utilization and it is possible to help a user to better manage an exercise schedule.

Figure 14:
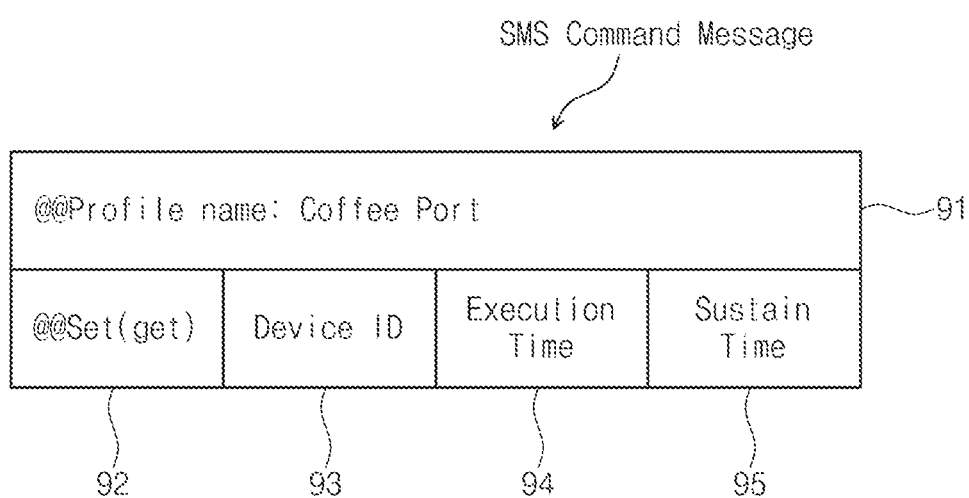
FIG. 14 shows an SMS command message transmitted to an external device configuring a user activity pattern management system according to an embodiment of the present invention.

FIG. 14 shows an SMS command message transmitted to an external device configuring a user activity pattern management system according to an embodiment of the present invention. Referring to FIG. 14, the SMS command message includes a meta script 91, a command 92, an ID 93 of the device 20 to be controlled, a control command execution time 94, and a sustain time. As an embodiment, the external device 130 may identify the meta script of the SMS command message and transmit a control command signal corresponding to a command to the portable terminal 120.

In an embodiment shown in FIG. 14, '@@' is used as an example of a meta script that may read the SMS command message, and 'set' or 'get' is used as a command. The 'set' is an example of a command representing that a schedule is modified on an external mobile terminal by using an SMS and the 'get' is an example of a command representing that a result processed according to a schedule is transmitted. However, according to a device to be controlled, the format of the SMS command message including a meta script or a command call may be variously changed.

The portable terminal 120 may modify a schedule management list, transmit a control message for automatically operating the device 20 to the terminal 110, or transmit user activity pattern data to the external device 130 or an external mobile terminal, according to a control command signal. According to an embodiment of the present invention, a guardian or a medical specialist may also control the portable terminal 120 or the device 20 remotely through an SMS message function.

Figure 15:
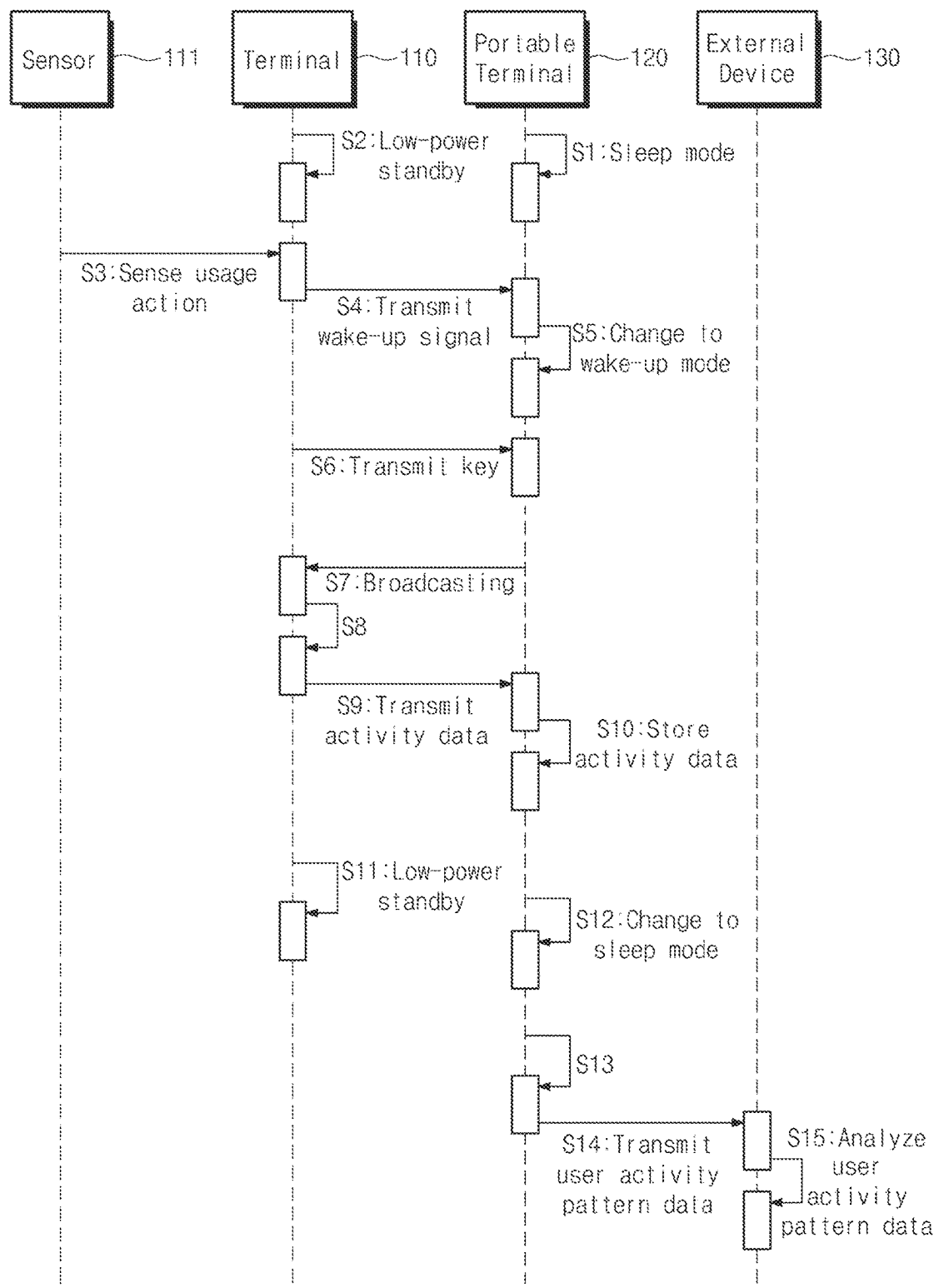
FIG. 15 is a flow chart for explaining a user activity pattern management method according to an embodiment of the present invention.

FIG. 15 is a flow chart for explaining a user activity pattern management method according to an embodiment of the present invention. Referring to FIGS. 5, 8, 9 and 15, when a user carrying the portable terminal 120 does not operate the device 20 as in steps 51 and S2, the portable terminal 120 operates in a sleep mode and the device 110 installed at the device 20 operates in a low-power standby mode to minimize power consumption of the portable terminal 120 and the terminal 110.

When a user operates the device 20, the sensor 111 of the terminal 110 senses a user's usage action and transmits a signal for waking up the terminal 110 to the control unit 112 of the terminal 110, in step S3, and accordingly, the power stage 114 operates the LF transmitter 113 by the control of the control unit 112 and performs LF short-range communication to transmit a wake-up signal to the portable terminal 120, in step S4.

By the wake-up signal from the terminal 110, the portable terminal 120 changes from the sleep mode to a wake-up mode in step S5. In step S6, the LF transmitter 113 of the terminal 110 transmits key information including an ID of the device 20 or an ID of the terminal 110 to the portable terminal 120 and in step S7, the portable terminal 120 broadcasts key information including the ID of the portable terminal 120 in response to key information. That is, the portable terminal 120 transmits its own ID value to all terminals 20 therearound in order to find a terminal, which transmits a signal to the portable terminal, among terminals.

The terminal 110 checks key information from the portable terminal 120 in step S8 and transmits activity data corresponding to a user's device 20 usage action to the portable terminal 120 in step S9. In step S10, the portable terminal 120 stores activity data received from the terminal 110 and collects user activity pattern data. In this case, the portable terminal 120 may include an ID of the portable terminal 120, activity data and operation time information on a device corresponding to activity data in one data packet to collect the user activity pattern data, so it is possible to raise .data utilization. Then, the terminal 110 changes back to the low-power standby mode in step S11 and the portable terminal 120 changes from the wake-up mode back to the sleep mode in step S12.

When in step S13, there is a user input or it is determined that the current time reaches a preset time, the portable terminal 120 transmits user activity pattern log data to the personal mobile terminal of a patient or guardian or an external device such as a hospital server in step S14. In step S15, the external device 130 may analyze user activity pattern log data transmitted from the portable terminal 120.

Although not shown in FIG. 15, the portable terminal 120 may provide a notification function at a time corresponding to each schedule on a schedule management list according to a preset schedule management list, through the display unit 121. The portable terminal 120 checks whether the user activity pattern data matches the schedule management list, senses an abnormal activity pattern that may cause a risky situation, and generates an alarm signal or transmit an alarm message to an external device 130 located in the activity area 10 or to a hospital server or the mobile terminal of a guardian located outside the activity area 10 when the user activity pattern data does not match the schedule management list or the abnormal activity pattern is sensed. When a schedule management message is transmitted from the external device 130, the portable terminal 12 may update the schedule management list.

In an embodiment of the present invention, the portable terminal 120 may check whether user activity pattern data matches a schedule management list and generate an alarm signal through the alarm generation unit 129 or transmit an alarm message to the mobile terminal of a guardian or a hospital server when the user activity pattern data does not match the schedule management list.

In an embodiment of the present invention, the portable terminal 120 may generate a wake-up event at a time set for each schedule on a schedule management list and change to a wake-up mode according to the wake-up event. In this case, the portable terminal 120 transmits a control message to the terminal 110 of a device 20 side corresponding to each schedule. The terminal 110 may receive a control message from the portable terminal 120, sense the approach of the portable terminal 120 and communicate with the control unit 30 of the device 20 through the communication interface 117 to automatically operate the device 20 according to the control message.

According to an embodiment of the present invention, if a user checks notification information provided according to a schedule management list by the portable terminal 120 and simply approaches the device 20 side according to a corresponding schedule, the operation of the device 20 is automatically performed according to a control message transmitted through wireless communication. Thus, it is possible to provide convenience for users who have difficulties in operating the device 20.

In an embodiment of the present invention, the external device 130 may receive an SMS command message from an external mobile terminal, read the SMS command message and transmit a corresponding control command signal to the portable terminal 120. The portable terminal 120 may modify a schedule management list, transmit a control message for automatically operating the device 20 to the terminal 110, or transmit user activity pattern data to the external device 130 or the external mobile terminal, according to the control command signal. According to an embodiment of the present invention, a guardian or a medical specialist may control the portable terminal 120 or the device 20 remotely through an SMS message function.

In an embodiment, by inputting a device or a measurement time to an SMS command message, it is also possible to receive only user activity pattern log data on a desired part. The portable terminal 120 receiving the SMS command message may search for data suitable for an option among accumulated user activity pattern log data the transmit the data to a personal mobile terminal, and the personal mobile terminal may transmit it to an external mobile terminal or a hospital server.

FIG. 16 is a flow chart of steps S13 and S14 shown in FIG. 15. Referring to FIG. 16, the portable module 120 activates or inactivates a wireless communication function in a preset cycle in steps S21, S27 and S29. When the wireless communication function is activated, the portable module 120 operates an advertisement function, transmits (broadcasts) a reception request message to the external device 130 and then ends the operation of the advertising function in steps S22 to S26, and S30 to S35).

When a corresponding application is executed by a user on the external device 130 such as a mobile terminal including a smart phone, signals around a user's mobile terminal are sensed therethrough, a reception request message is scanned and then the operation is ended in steps S28, S33 and S34. Next, in device connection step S36, the external device 130 senses a signal transmitted by the portable terminal 120, a user is identified through an ID of the signal, and an acknowledgement message is transmitted from the external device 130 to the portable terminal 120, and in this process, a wireless network is set between the portable terminal 120 and the external device 130.

When the wireless network is set between the portable terminal 120 and the external device 130, user activity pattern data accumulated so far is transmitted to the external device 130. That is, when the wireless network is not set between the portable terminal 120 and the external device 130, for example, when the wireless communication function is inactivated or when the wireless communication function is activated but an acknowledgment message corresponding to a reception request message is not transmitted from the external device 130, the processor 122 of the portable terminal 120 stores user activity pattern data in the memory unit 128 by utilizing the concept of "delay-tolerant" and then transmits user activity pattern data stored in steps S37 to S39 when the wireless network is set between the portable terminal and the external device 130. Accordingly, a user, a guardian or a medical team may see user activity pattern data through the external device 130.

Since the above embodiments are presented to help the understanding of the present invention, it should be understood that they do not limit the scope of the present invention and various variations thereto also belong to the scope of the present invention. The technical protective scope of the present invention should be defined by the technical spirit of the following claims and it should be understood that the technical protective scope of the present invention is not limited to the wording of the claims but actually reaches inventions having equivalent technical values. It is true that a person skilled in the art may implement various variations and imitations without departing from the technical spirit of the present invention.

What is claimed is:

1. A user's daily activity logging and analyzing system comprising:
 a terminal installed at each of devices provided in a user activity area, the terminal comprising a sensor sensing a user's usage action to each device; and
 a portable terminal receiving activity data corresponding to the usage action from the terminal to construct user activity pattern data,
 wherein the terminal comprises a low frequency (LF) transmitter that transmits a wake-up signal to the portable terminal when the usage action is sensed,
 wherein the portable terminal comprises:
  a LF receiver that receives the wake-up signal from the LF transmitter, and changes from a sleep mode to a wake-up mode according to the wake-up signal to receive the activity data from the terminal; and
  a schedule management unit that generates a wake-up event at a time corresponding to each schedule on a preset schedule management list,
 wherein the portable terminal changes to the wake-up mode according to the wake-up event to transmit a control message for automatic operation of a device corresponding to each schedule to the terminal installed at the device, and
 wherein the terminal receives the control message, and senses an approach of the portable terminal to communicate with the device at which the terminal is installed and automatically operate the device corresponding to each schedule, according to the control message.

2. The user's daily activity logging and analyzing system of claim 1, wherein the terminal operates in a low-power standby mode after the activity data is transmitted to the portable terminal until a new usage action is sensed, and the portable terminal changes from the wake-up mode to the sleep mode after the activity data is received from the terminal.

3. The user's daily activity logging and analyzing system of claim 1, wherein the sensor comprises at least one selected from a hall sensor, a piezo sensor, a photo sensor, a loadcell, a thermal sensor, an angular sensor, and an ammeter.

4. The user's daily activity logging and analyzing system of claim 1, wherein the portable terminal further comprises:
 a time measurement module measuring time information; and
 a processor combining an ID of the portable terminal, the activity data, and time information corresponding to the activity data, in one data packet to constructing the user activity pattern data.

5. The user's daily activity logging and analyzing system of claim 4, wherein the portable terminal further comprises a wireless communication unit broadcasting request data comprising the ID of the portable terminal in the wake-up mode, and
 the terminal further comprises a wireless transmission unit transmitting the activity data to the portable terminal in response to the request data.

6. The user's daily activity logging and analyzing system of claim 5, wherein the portable terminal further comprises a state control unit activating or deactivating a wireless communication function of the wireless communication unit in a preset cycle, and the wireless communication unit broadcasts a reception request message while the wireless communication function is activated, sets a wireless network in response to an acknowledgement message from an external device corresponding to the reception request message and transmits the user activity pattern data to the external device.

7. The user's daily activity logging and analyzing system of claim 6, wherein the wireless communication unit receives a schedule management message from the external device, and
 the schedule management unit updates the schedule management list according to the schedule management message.

8. The user's daily activity logging and analyzing system of claim 6, wherein the processor checks whether the user activity pattern data matches the schedule management list, and generates an alarm signal or transmits an alarm message to the external device by controlling the wireless communication unit when the user activity pattern data does not match the schedule management list or an abnormal activity pattern is sensed.

9. The user's daily activity logging and analyzing system of claim 8, wherein the external device receives an SMS command message from an external mobile terminal, reads the SMS command message and transmits a corresponding control command signal to the portable terminal.

10. The user's daily activity logging and analyzing system of claim 9, wherein the SMS command message comprises a meta script, a command, an ID of a device to be controlled, and a control command execution time, and the external device identifies the meta script and transmits the control command signal corresponding to the command to the portable terminal.

11. The user's daily activity logging and analyzing system of claim 10, wherein the portable terminal modifies the schedule management list, transmits the control message for automatically operating the device to the terminal, or transmits the user activity pattern data to the external device or the external mobile terminal, according to the control command signal.

12. A user's daily activity logging and analyzing device comprising:
 a portable terminal receiving activity data corresponding to a user's usage action to a device from a terminal installed at each of devices provided in a user activity area and constructing user activity pattern data, the portable terminal receiving a wake-up signal corresponding to the usage action from the terminal installed at a device which the user's usage action is sensed, changing from a sleep mode to a wake-up mode according to the wake-up signal and receiving the activity data from the terminal installed at the device which the user's usage action is sensed,
 wherein the portable terminal comprises a schedule management unit that generates a wake-up event at a time corresponding to each schedule on a preset schedule management list,
 wherein the portable terminal changes to the wake-up mode according to the wake-up event to transmit a control message to the terminal to automatically operate a device corresponding to each schedule when an approach of the portable terminal is sensed by the terminal installed at the device.

13. The user's daily activity logging and analyzing device of claim 12, wherein the portable terminal checks whether the user activity pattern data matches the preset schedule management list, and generates an alarm signal or transmits an alarm message to an external device when the user activity pattern data does not match the schedule management list or an abnormal activity pattern is sensed.

14. A method of logging and analyzing a user's daily activity history, the method comprising:
- sensing a user's usage action to devices, the devices being provided in a user activity area, to transmit a wake-up signal to a portable terminal;
- changing the portable terminal from a sleep mode to a wake-up mode according to the wake-up signal;
- transmitting activity data corresponding to the user's usage action from a terminal installed at a device which the user's usage action is sensed to the portable terminal;
- constructing user activity pattern data using the activity data by the portable terminal;
- generating, by the portable terminal, a wake-up event at a time corresponding to each schedule on a preset schedule management list;
- changing the portable terminal to the wake-up mode according to the wake-up event and transmitting a control message for automatic operation of the device corresponding to each schedule to the terminal installed at the device; and
- by the terminal installed at the device corresponding to each schedule, receiving the control message from the portable terminal, and sensing an approach of the portable terminal to communicate with the device corresponding to each schedule and to automatically operate the device, according to the control message.

15. The method of claim 14, further comprising:
- checking by the portable terminal whether the user activity pattern data matches the preset schedule management list;
- sensing an abnormal activity pattern; and
- generating an alarm signal or transmitting an alarm message to an external device, when the user activity pattern data does not match the preset schedule management list or the abnormal activity pattern is sensed.

16. The method of claim 14, further comprising:
- receiving, by the external device, an SMS command message comprising a meta script and a command from an external mobile terminal;
- identifying the meta script and transmitting a control command signal corresponding to the command to the portable terminal, by the external device; and
- modifying the schedule management list, or transmitting the user activity pattern data to the external device or the external mobile terminal, by the portable terminal, according to the control command signal.

* * * * *